United States Patent [19]

Maravetz

[11] Patent Number: 4,702,763
[45] Date of Patent: Oct. 27, 1987

[54] HERBICIDAL 1-ARYL-DELTA2-1,2,4-TRIAZOLIN-5-ONES

[75] Inventor: Lester L. Maravetz, Westfield, N.J.

[73] Assignee: FMC Corporation, Philadelphia, Pa.

[21] Appl. No.: 834,157

[22] Filed: Feb. 27, 1986

Related U.S. Application Data

[63] Continuation-in-part of Ser. No. 655,960, Sep. 28, 1984, abandoned, which is a continuation-in-part of Ser. No. 541,596, Oct. 13, 1983, abandoned.

[51] Int. Cl.$^4$ ................ C07D 249/12; A01N 43/653
[52] U.S. Cl. ........................................ 71/90; 71/91; 71/92; 548/263
[58] Field of Search ............... 71/88, 92, 91, 90; 548/263, 264, 265

[56] References Cited

PUBLICATIONS

Dupont, Derwent Absa. 18116; EP 46–677 (3.03.82).

*Primary Examiner*—Glennon H. Hollrah
*Assistant Examiner*—D. L. Dinner
*Attorney, Agent, or Firm*—Robert M. Kennedy; H. Robinson Ertelt

[57] ABSTRACT

Aryltriazolinones of the formula

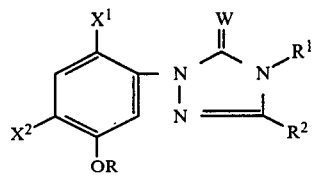

in which W is oxygen or sulfur; $X^1$ and $X^2$ are independently selected from halogen, haloalkyl, and alkyl; R is a three- to eight-membered ring heterocyclic group of one or two, same or different, ring heteroatoms selected from oxygen, sulfur, and nitrogen, or an alkyl radical substituted with said heterocyclic group; $R^1$ is alkyl, haloalkyl, cyanoalkyl, alkenyl, alkynyl, or a group of the formula -alkyl-Y—$R^3$; $R^2$ is halogen, alkyl, cyanoalkyl, haloalkyl, arylalkyl, or a group of the formula -alkyl-Y—$R^3$; $R^3$ is alkyl, alkenyl, or alkynyl; and Y is oxygen or S(O)$_r$ in which r is 0 to 2 are disclosed and exemplified.

8 Claims, No Drawings

HERBICIDAL 1-ARYL-DELTA2-1,2,4-TRIAZOLIN-5-ONES

This application is a continuation-in-part of application Ser. No. 655,960, filed 9/28/84, now abandoned, which is a continuation-in-part of U.S. Application Ser. No. 541,596, now abandoned filed Oct. 13, 1983, incorporated herein by reference.

The invention described in this application pertains to weed control in agriculture, horticulture, or other fields where there is a desire to control unwanted plant growth. More specifically, the present application describes a series of novel herbicidal 1-aryl-$\Delta^2$-1,2,4-triazolin-5-ones and 5-thiones, herbicidal compositions of them, methods of preparing them, and methods for preventing or destroying undesired plant growth by preemergence or postemergence application of the herbicidal compositions to the locus where control is desired. The present compounds may be used to effectively control a variety of both grassy and broad-leaf plant species. The present invention is particularly useful in agriculture, as a number of the novel arylthiazolinones described herein show a selectivity favorable to soybean, corn, cotton, wheat, rice, sunflower, or other crops at application levels which inhibit the growth of or destroy a variety of weeds.

Various herbicidal 1-aryl-$\Delta^2$-1,2,4-triazolin-5-ones are known in the art. U.S. Pat. No. 4,318,731 and corresponding British Pat. No. 2,056,971 disclose herbicidal aryltriazolinones of the formula

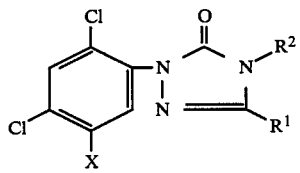

wherein $R^1$ is alkyl, $R^2$ is hydrogen, alkyl, or alkenyl, and X is hydroxy, alkyl, alkoxy, alkoxyalkoxy, alkenyloxy, or alkoxycarbonylalkyloxy.

British Pat. No. 2,090,250, a continuation-in-part of the above British patent, adds to the above genus compounds wherein $R^2$ is alkynyl, halomethyl, or haloethyl, and X is alkoxy, alkenyloxy, alkynyloxy, alkoxyalkoxy, hydroxy, halomethyloxy, or haloethyloxy.

European Patent Application Publication No. 55,105 discloses a series of herbicidal aryltriazolinones of the formula

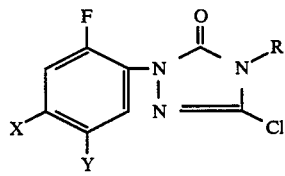

wherein R is alkyl, alkenyl, or cycloalkyl, X is chlorine or bromine, and Y is hydrogen or alkoxy.

Japanese Kokai No. 81-32,468 discloses herbicidal aryltriazolinones of the formula

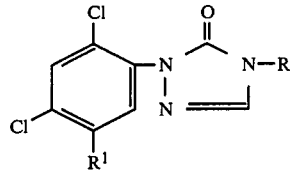

wherein R is hydrogen, alkyl, or 2-propenyl, and $R^1$ is methyl or alkoxy.

South African Patent Application No. 78/3182 discloses herbicidal arylthiazolinones of the formula

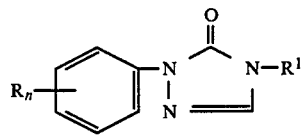

wherein $R_n$ is hydrogen or represents 1 to 4 same or different radicals selected from halogen, nitro, cyano, optionally halosubstituted alkyl, alkoxy, or alkylthio, and optionally substituted phenyl or phenoxy, and $R^1$ is alkyl, alkoxyalkyl, dialkoxyethyl, dialkylaminoethyl, or cycloalkyl.

U.S. Pat. No. 4,315,767 discloses herbicidal bicyclic compounds of the following formula

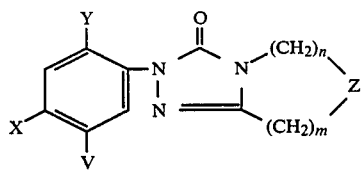

wherein V is hydrogen, halogen, methyl, or alkoxy, X is hydrogen, halogen, cyano, methyl, methoxy, or nitro, Y is hydrogen, halogen, or methyl, m and n are 0 to 4 (m plus n is 2 to 4), Q is oxygen or sulfur, and Z is oxygen, $S(O)_p$, or $NR^1$ wherein p is 0–2 and $R^1$ is alkyl, provided that when m plus n is 2 or 4 then Y and X are other than hydrogen, and when Z is $S(O)_p$ then n is 1 to 4.

Additional herbicidal bicyclic compounds based on aryltriazolinones are disclosed in U.S. Pat. No. 4,213,773 and have the following structural formula

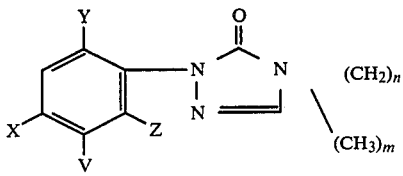

wherein V is hydrogen, halogen, hydroxy, alkyl, or —$OR^1$; $R^1$ is optionally substituted alkyl, cycloalkyl, cycloalkylalkyl, optionally substituted alkenyl, alkynyl, optionally substituted benzyl, alkylaminocarbonyl, (alkyl)(methyl or methoxy)aminocarbonyl, acyl, alkoxycarbonyl, or —$CHR^7R^8$ wherein $R^7$ is hydrogen or alkyl and $R^8$ is cyano, acetyl, hydroxycarbonyl, alkoxycarbonyl, hydroxymethyl, alkoxymethyl, alkylcarbonyloxymethyl, hydroxycarbonylethenyl, alkoxycarbonylethenyl, or a group —CO—$NR^{11}R^{12}$ wherein $R^{11}$ is hydrogen, alkyl, alkenyl, or alkoxy, and $R^{12}$ is hydrogen or alkyl; X is halogen, cyano, methyl, methoxy, or nitro; Y is hydrogen, halogen, or methyl; Z is hydrogen or halogen; n is 3–5; m is 0–2; and Q is oxygen or sulfur, with certain provisos.

A class of Δ²-1,2,4-triazolin-5-ones is disclosed as fungicides in U.S. Pat. No. 4,098,896. The disclosed genus has the formula

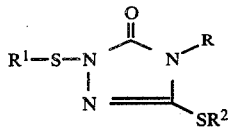

wherein R is alkyl, alkenyl, alkynyl, cycloalkyl, or optionally substituted phenyl or arylalkyl, $R^1$ is haloalkyl or haloalkenyl, and $R^2$ is optionally substituted alkyl, alkenyl, or alkynyl, or optionally substituted aryl, arylalkyl, or alkylaryl.

The present application describes a novel class of herbicidal 1-aryl-Δ²-1,2,4-triazolin-5-ones and 5-thiones characterized primarily in that the 1-aryl moiety is a 2,4,5-trisubstituted-phenyl group in which the C-5 substituent is a group —OR wherein R is an oxygen-, sulfur- or nitrogen-containing heterocycle or an alkyl group substituted therewith.

Any alkyl, alkenyl, or alkynyl group herein or the alkyl, alkenyl, or alkynyl portion of any group may be a straight chain or branched chain radical. Thus, 1-methylethyl, methylcyclopropyl, 2-methyl-2-propenyl, and 1-methyl-2-propynyl are branched chain examples of alkyl, cyclic alkyl, alkenyl, and alkynyl radicals respectively. Any halogen may be fluorine, chlorine, or bromine. Haloalkyl, haloalkenyl, and haloalkynyl radicals may have one or more same or different halogen atoms. Any aryl group or the aryl portion of any group may be a hydrocarbyl group such as phenyl or it may contain one or more heteroatoms such as in thienyl or furyl. Any aryl may be substituted, for example, with halogen or alkyl of 1 to 4 carbon atoms.

The compounds of this invention have the formula

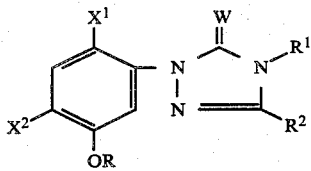

in which $X^1$ and $X^2$ are independently selected from halogen, haloalkyl, and alkyl;

W is oxygen or sulfur;

R is a three- to eight-membered ring heterocyclic group of one or two, same or different, ring heteroatoms selected from oxygen, sulfur, and nitrogen, or an alkyl radical substituted with said heterocyclic group;

$R^1$ is alkyl, haloalkyl, cyanoalkyl, alkenyl, alkynyl, or a group of the formula —alkyl—Y—$R^3$;

$R^2$ is halogen, alkyl, cyanoalkyl, haloalkyl, arylalkyl, or a group of the formula —alkyl—Y—$R^3$;

$R^3$ is alkyl, alkenyl, or alkynyl; and Y is oxygen or $S(O)_4$ in which r is 0 to 2.

The R substituent heterocyclic group may be saturated, unsaturated, or aromatic. It may be substituted with halogen, alkyl, or haloalkyl, or it may be adjoined to a benzene ring at two adjacent ring carbon atoms to form a benzoheterocycle bicyclic group, the two adjacent ring carbon atoms being common to both the heterocyclic ring and the benzene ring. In sulfur-containing heterocycles, the sulfur may be present in divalent form or as the S-oxide or S-dioxide.

One aspect of the present invention comprises the compounds of formula I above wherein R is an optionally substituted and optionally benzene-adjoined nitrogen-containing heterocycle or an alkyl radical of 1 to 5 carbon atoms substituted with said heterocycle. Preferably, the R substituent for this group of compounds is a non-aromatic heterocycle, preferably containing only one nitrogen atom and no other heteroatoms, the nitrogen atom preferably being substituted with an alkyl group of 1 to 5 carbon atoms, particularly a methyl group. This aspect of the invention is exemplified herein by compounds 29 and 31 below wherein R is 1-methyl-3-pyrrolidinyl.

A second aspect of the present invention comprises the compounds of formula I above wherein R is an aromatic, optionally substituted and optionally benzene-adjoined, oxygen- or sulfur-containing heterocycle or an alkyl group of 1 to 5 carbon atoms substituted therewith. Preferably, R is an optionally substituted furanyl, furanylalkyl, thienyl, or thienylalkyl radical. In the exemplary compounds 10 and 11 below, R is furfuryl and 2-thienylmethyl respectively.

A further aspect of the present invention comprises the compounds of formula I above wherein R is a non-aromatic, optionally substituted and optionally benzene-adjoined, oxygen- or sulfur-containing heterocycle or an alkyl group of 1 to 5 carbon atoms substituted therewith. This group of compounds represents a preferred embodiment of the present invention. The R substituent heterocycle is preferably saturated, but may be unsaturated, and is preferably unsubstituted or substituted with alkyl of 1 to 5 carbon atoms, particularly methyl, or it may be substituted with halogen such as fluorine, chlorine, or bromine or haloalkyl of 1 to 5 carbon atoms, for example, chlorodifluoromethyl. Where the R heterocycle contains two ring heteroatoms, they may be the same or different, oxygen or sulfur, preferably the same, and are separated from each other in the ring by at least one carbon atom. In sulfur-containing heterocycles, the sulfur may be present in divalent form or as the S-oxide or S-dioxide. The R substituent heterocycle for these compounds of the invention will be recognized as being a cyclic ether or thioether or an S-oxide or S-dioxide derivative of a cyclic thioether. Examples of R groups for this subgenus are 3-tetrahydrofuranyl, tetrahydrofurfuryl, tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran-4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahydrothien-3-yl, 2,2-dimethyl-1,1,3,3-tetraoxo-1,3-dithiolan-4-ylmethyl, and 1,1-dioxotetrahydro-4H-thiopyran-4-yl. Additional examples include 1,4-dithiacycloheptan-6-yl, 1,4-dithiacyclohept-5-ene-6-yl, tetrahydro-4H-pyran-3-yl, glycidyl, 2,3-epithiopropyl, and 2,2-bis(chlorodifluoromethyl)-1,3-dioxolan-4-ylmethyl.

Of especial interest is the genus comprising the compounds of formula I above in which $X^1$ and $X^2$ are independently selected from halogen, haloalkyl of 1 to 3 carbon atoms, and alkyl of 1 to 5 carbon atoms;

W is sulfur or, preferably, oxygen;

R is 1-methyl-3-pyrrolidinyl, furfuryl or 2-thienylmethyl, or preferably 3-tetrahydrofuranyl, tetrahydrofurfuryl, tetrahydropyran-2-ylmethyl, 1,3-dioxolan-2-yl-methyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran-4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahyrothien-3-yl, 2,2-dimethyl-1,1,3,3-tetraoxo-1,3-dithiolan-4-ylmethyl, 1,4-dithiacycloheptan-6-yl, 1,4-dithiacyclohept-5-ene-6-yl, tetrahydro-4H-pyran-3-yl, glycidyl, 2,3-epithiopropyl, 2,2-bis(chlorodifluoromethyl)-1,3-dioxolan-4-ylmethyl, or 1,1-dioxotetrahydro-4H-thiopyran-4-yl;

$R^1$ is alkyl, haloalkyl, or cyanoalkyl of 1 to 5 alkyl carbon atoms, alkenyl or alkynyl of 2 to 5 carbon atoms, or a group $(CH_2)_n$—Y—$R^3$ wherein n is 1 to 5;

$R^2$ is halogen, alkyl, haloalkyl, cyanoalkyl, or arylalkyl wherein each alkyl is of 1 to 5 carbon atoms, or a group $(CH_2)_n$—Y—$R^3$ wherein n is 1 to 5;

$R^3$ is alkyl of 1 to 5 carbon atoms or alkenyl or alkynyl of 2 to 5 carbon atoms; and Y is oxygen or $S(O)_r$ in which r is 0 to 2.

The substituents $X^1$ and $X^2$ may be the same, and in some instances each will usually be a fluorine, chlorine, or bromine atom (preferably chlorine); less frequently, a methyl group. When $X^1$ and $X^2$ are different, $X^1$ will advantageously be fluorine or chlorine, preferably fluorine, and $X^2$ will frequently be selected from among chlorine, bromine, haloalkyl such as difluoromethyl, and alkyl such as methyl. $X^2$ is preferably chlorine.

The $R^1$ substituent is preferably a haloalkyl radical of 1 to 3 carbon atoms and having one or more independently selected halogen atoms, preferably selected from fluorine and chlorine; more preferably, a fluoroalkyl radical such as 3-fluoropropyl or, especially, difluoromethyl. Other $R^1$ substituents of particular interest include alkyl of 1 to 5 (preferably 1 to 3) carbon atoms such as n-propyl, cyanoalkyl of 1 to 3 alkyl carbon atoms such as cyanomethyl, alkenyl of 2 to 5 (preferably 3 to 5) carbon atoms especially 2-propenyl, alkynyl of 2 to 5 (preferably 3 to 5) carbon atoms such s 2-propynyl, or a group —$(CH_2)_2$—Y—$R^3$ in which Y is oxygen or sulfur and $R^3$ is alkyl of 1 to 5 (especially 1 or 2) carbon atoms such as methyl. Frequently $R^1$ will be selected from n-propyl difluoromethyl, 3-fluoropropyl, cyanomethyl, and 2-propenyl.

$R^2$ is preferably alkyl of 1 to 5 (more preferably 1 to 3) carbon atoms, especially methyl; haloalkyl of 1 to 3 carbon atoms, particularly a fluoroalkyl such as fluoromethyl or difluoromethyl; cyanoalkyl of 1 to 3 alkyl carbon atoms, for example, cyanomethyl; benzyl; or a group —$(CH_2)_n$—Y—$R^3$ in which n is 1 or 2, Y is oxygen or sulfur, and $R^3$ is alkyl of 1 to 5 carbon atoms such as methyl or ethyl. $R^2$ will frequently and advantageously be fluoromethyl, difluoromethyl, or, especially, unsubstituted methyl.

Compounds in which the R substituent is 3-tetrahydrofuranyl, tetrahydrofurfuryl, or 1,1-dioxotetrahydrothien-3-yl, particularly 3-tetrahydrofuranyl, generally show very high herbicidal activity, especially where preferred groups are selected for the other substituents. Other preferred radicals for R include: tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 1,3-dioxan-4-methyl, tetrahydro-4H-pyran-4-yl, tetrahydrothien-3-yl, and 1-oxotetrahydrothien-3-yl. Also of particular interest are compounds wherein R is 3-(2-methyl-1,3-dioxolan-2-yl)propyl, 5,6-dihydro-2H-pyran-3-ylmethyl, 2,2-dimethyl-1,3-dithiolan-4-ylmethyl, or tetrahydro-4H-thiopyran-4-yl.

The present compounds may generally be prepared by reaction of an appropriately substituted 5-hydroxyphenyltriazolinone (01a) or the thione analog (01b) with R—X, wherein X is a good leaving group, in the presence of a base as illustrated in the following equation.

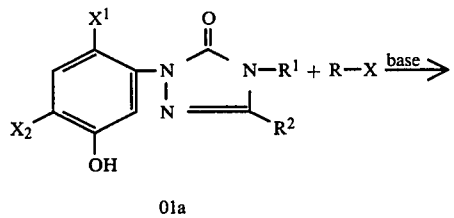

01a

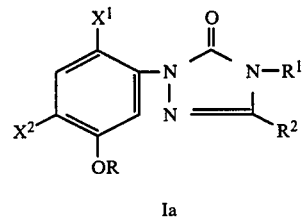

Ia

Satisfactory results have been obtained with sodium hydride base in dimethylformamide for reactions in which the leaving group X is 4-methylphenylsulfonyloxy, bromine, or chlorine.

The present compounds containing a sulfinyl or a sulfonyl group in R, $R^1$, or $R^2$ may be prepared by oxidation of the corresponding thio compound, generally with hydrogen peroxide, as described in detail in Examples 25, 26, 27, and 34 below for certain R groups.

The aryltriazolin-5-thiones (W is sulfur) may be prepared by methods within the skill of the art, for example, by treating an appropriately substituted aryltriazolin-5-one with phosphorus pentasulfide in toluene under reflux conditions. The C═O to C═S conversion step may be conducted prior to subsequent to the addition of the $R^1$ substituent to the heterocyclic ring.

The intermediates R—X and 01a are either known in the art and, therefore, are available by known methods, or may be prepared by methods analogous or similar to known methods or by methods within the skill of the art. For example, U.S. Pat. No. 4,318,731 and British Pat. No. 2,090,250 disclose preparation of a number of the present hydroxyphenyl intermediates 01a wherein $X^1$ and $X^2$ are chlorine atoms by dealkylation of the corresponding alkyloxyphenyl or alkenyloxyphenyl compound. Many of the hydroxyphenyl intermediates 01a for the present exemplary compounds were prepared by dealkylation of the corresponding isopropoxy or methoxy compound in the presence of concentrated sulfuric acid, a mixture of hydrobromic and acetic acids, or boron tribromide.

Further methods for preparing intermediate compounds are illustrated in the following chemical equations in which steps A and B are analogous to the method of U.S. Pat. No. 3,290,327, issued Dec. 6, 1966, incorporated herein by reference.

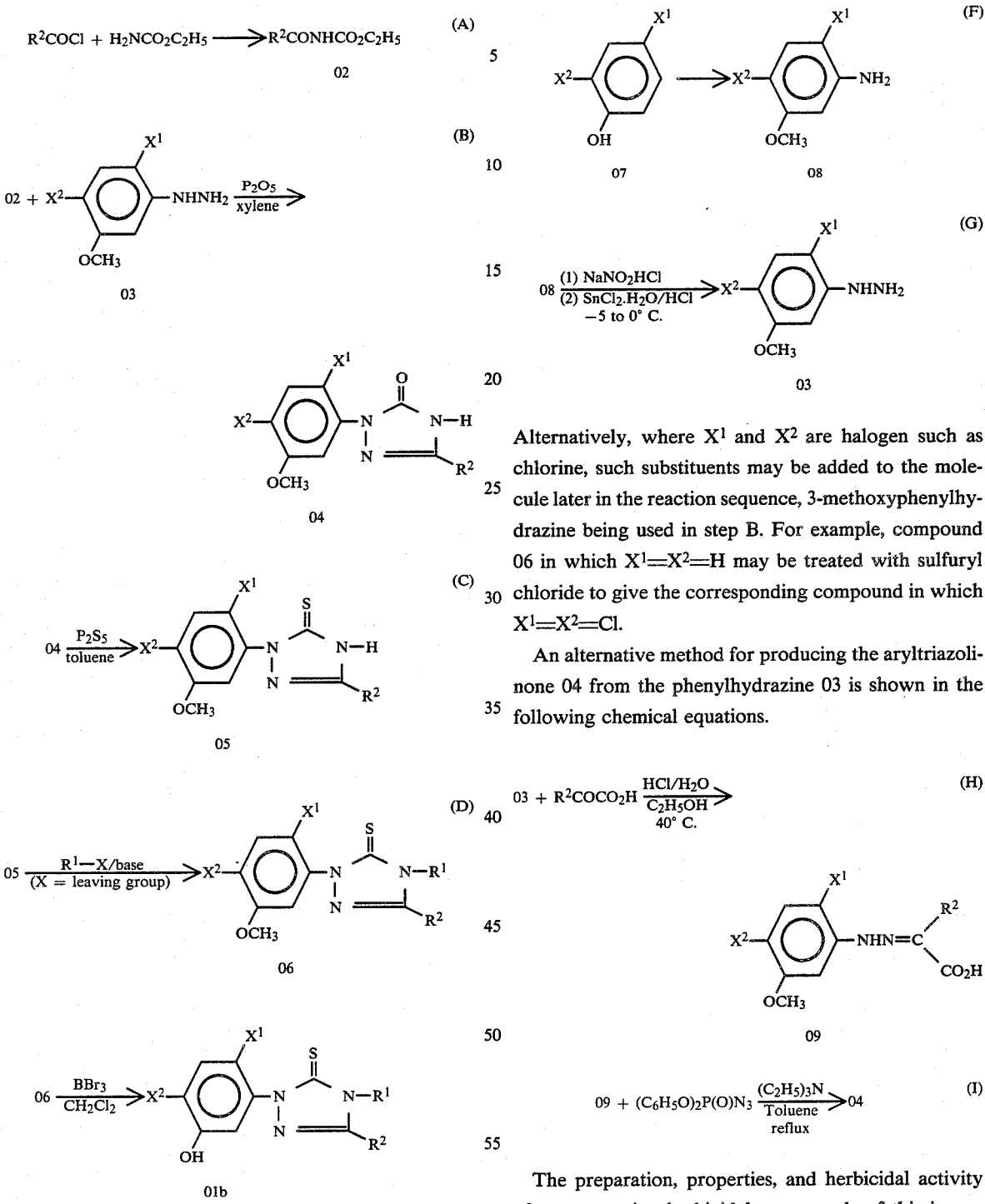

Phenylhydrazines (03) useful in step B above may be prepared by the method shown in the following chemical equations in which step F itself represents a 5-step conversion and is analogous to the method of E. Nagano et al., European Patent Application No. 69,855, incorporated herein by reference.

Alternatively, where $X^1$ and $X^2$ are halogen such as chlorine, such substituents may be added to the molecule later in the reaction sequence, 3-methoxyphenylhydrazine being used in step B. For example, compound 06 in which $X^1=X^2=H$ may be treated with sulfuryl chloride to give the corresponding compound in which $X^1=X^2=Cl$.

An alternative method for producing the aryltriazolinone 04 from the phenylhydrazine 03 is shown in the following chemical equations.

The preparation, properties, and herbicidal activity of representative herbicidal compounds of this invention are illustrated further in the examples below. All temperatures shown are in degrees Celsius, and all pressures are in mm Hg.

Representative compounds of the invention are identified by chemical structure in the following table wherein the compound numbers correspond to Example numbers.

TABLE 1
Representative Compounds

| Cpd. No. | $X^1$ | $X^2$ | R | $R^1$ | $R^2$ | W |
|---|---|---|---|---|---|---|
| 1 | Cl | Cl | tetrahydrofuran-3-yl | $CF_2H$ | $CH_3$ | O |
| 2 | Cl | Cl | (tetrahydrofuran-2-yl)methyl | $CF_2H$ | $CH_3$ | O |
| 3 | Cl | Cl | (tetrahydrofuran-2-yl)methyl | $CH_2CH=CH_2$ | $CH_3$ | O |
| 4 | Cl | Cl | (tetrahydropyran-2-yl)methyl | $CF_2H$ | $CH_3$ | O |
| 5 | Cl | Cl | (tetrahydropyran-2-yl)methyl | $CH_2CH=CH_2$ | $CH_3$ | O |
| 6 | Cl | Cl | (1,3-dioxolan-2-yl)methyl | $CF_2H$ | $CH_3$ | O |
| 7 | Cl | Cl | 2-(1,3-dioxolan-2-yl)ethyl | $CF_2H$ | $CH_3$ | O |
| 8 | Cl | Cl | (2,2-dimethyl-1,3-dioxolan-4-yl)methyl | $CF_2H$ | $CH_3$ | O |
| 9 | Cl | Cl | 3-(2-methyl-1,3-dioxolan-2-yl)propyl | $CF_2H$ | $CH_3$ | O |
| 10 | Cl | Cl | furan-2-ylmethyl | $CF_2H$ | $CH_3$ | O |
| 11 | Cl | Cl | thien-2-ylmethyl | $CF_2H$ | $CH_3$ | O |
| 12 | Cl | Cl | (1,3-dioxan-4-yl)methyl | $CF_2H$ | $CH_3$ | O |

TABLE 1-continued

Representative Compounds

[Structure: benzene ring with X¹, X², OR substituents, connected to N-N=C(W)-N(R¹)-C(R²)= group]

| Cpd. No. | X¹ | X² | R | R¹ | R² | W |
|---|---|---|---|---|---|---|
| 13 | Cl | Cl | CH₂-(1,4-benzodioxan-2-yl) | CF₂H | CH₃ | O |
| 14 | Cl | Cl | tetrahydropyran-4-yl | CF₂H | CH₃ | O |
| 15 | Cl | Cl | CH₂-(3,6-dihydro-2H-pyran-3-yl) | CF₂H | CH₃ | O |
| 16 | Cl | Cl | CH₂-(1,3-dioxolan-2-yl) | CH₂CH=CH₂ | CH₃ | O |
| 17 | Cl | Cl | tetrahydrofuran-3-yl | CH₂CH=CH₂ | CH₃ | O |
| 18 | Cl | Cl | tetrahydrofuran-3-yl | n-C₃H₇ | CH₃ | O |
| 19 | Cl | Cl | CH₂-(tetrahydrofuran-2-yl) | n-C₃H₇ | CH₃ | O |
| 20 | Cl | Cl | CH₂-CH(S-C(CH₃)₃)(S-) (dithiolane) | CF₂H | CH₃ | O |
| 21 | Cl | Cl | tetrahydrothiopyran-4-yl | CF₃H | CH₃ | O |
| 22 | Br | Br | tetrahydrofuran-3-yl | CF₂H | CH₃ | O |
| 23 | Br | Br | CH₂-(tetrahydrofuran-2-yl) | CF₂H | CH₃ | O |
| 24 | Cl | Cl | tetrahydrothiophen-3-yl | CF₂H | CH₃ | O |

TABLE 1-continued

Representative Compounds

[Structure: aryl group with X¹, X², OR substituents connected via N-N=C(R²) and N(R¹)-C(=W) groups]

| Cpd. No. | X¹ | X² | R | R¹ | R² | W |
|---|---|---|---|---|---|---|
| 25 | Cl | Cl | tetrahydrothiophene-SO (3-yl) | CF₂H | CH₃ | O |
| 26 | Cl | Cl | tetrahydrothiophene-SO₂ (3-yl) | CF₂H | CH₃ | O |
| 27 | Cl | Cl | CH₂—C(SO₂—C(CH₃)₃)(SO₂—) | CF₂H | CH₃ | O |
| 28 | Cl | CH₃ | tetrahydrothiopyran-4-yl | CF₂H | CH₃ | O |
| 29 | Br | Br | N-methylpyrrolidin-3-yl | CF₂H | CH₃ | O |
| 30 | Br | Br | tetrahydrofuran-3-yl | CF₂H | CH₃ | O |
| 31 | Cl | Cl | N-methylpyrrolidin-3-yl | CF₂H | CH₃ | O |
| 32 | Cl | CH₃ | tetrahydrofuran-3-yl | CF₂H | CH₃ | O |
| 33 | Cl | CH₃ | CH₂-tetrahydrofuran-2-yl | CF₂H | CH₃ | O |
| 34 | Cl | Cl | tetrahydrothiopyran-4-yl SO₂ | CF₂H | CH₃ | O |
| 35 | Cl | Cl | tetrahydrofuran-3-yl | CH₂CH=CH₂ | Cl | O |
| 36 | Cl | Cl | tetrahydrofuran-3-yl | CF₂H | C₂H₅ | O |

TABLE 1-continued
Representative Compounds
| Cpd. No. | X¹ | X² | R | R¹ | R² | W |
|---|---|---|---|---|---|---|
| 37 | Cl | Cl |  | $CF_2H$ | $C(CH_3)_3$ | O |
| 38 | F | Cl | 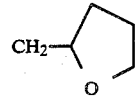 | $CF_2H$ | $CH_3$ | O |
| 39 | F | Cl | 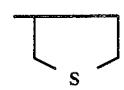 | $CF_2H$ | $CH_3$ | O |
| 40 | F | Cl | 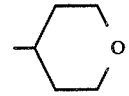 | $CF_2H$ | $CH_3$ | O |
| 41 | F | Cl | 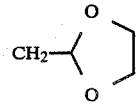 | $CF_2H$ | $CH_3$ | O |
| 42 | F | Cl | 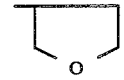 | $CF_2H$ | $CH_3$ | O |
| 43 | Cl | F | 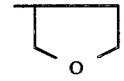 | $CF_2H$ | $CH_3$ | O |
| 44 | F | F | 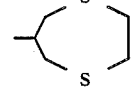 | $CF_2H$ | $CH_3$ | O |
| 45 | F | Cl | 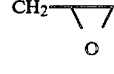 | $CF_2H$ | $CH_3$ | O |
| 46 | F | Cl | 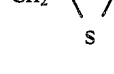 | $CF_2H$ | $CH_3$ | O |
| 47 | F | Cl | 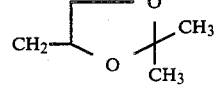 | $CF_2H$ | $CH_3$ | O |
| 48 | F | Cl |  | $CF_2H$ | $CH_3$ | O |

TABLE 1-continued
Representative Compounds
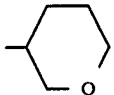
| Cpd. No. | X¹ | X² | R | R¹ | R² | W |
|---|---|---|---|---|---|---|
| 49 | F | Cl | 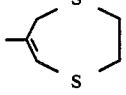 | $CF_2H$ | $CH_3$ | O |
| 50 | F | Cl | 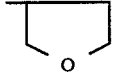 | $CF_2H$ | $CH_3$ | O |
| 51 | F | Cl | 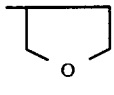 | $CFH_2$ | $CH_3$ | O |
| 52 | F | Cl | 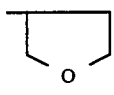 | $(CH_2)_3F$ | $CH_3$ | O |
| 53 | F | Cl | 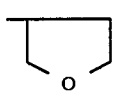 | $CH_2C{\equiv}CH$ | $CH_3$ | O |
| 54 | F | Cl | 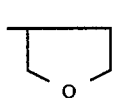 | $(CH_2)_2OCH_3$ | $CH_3$ | O |
| 55 | F | Cl | 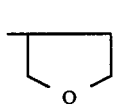 | $CF_2H$ | $CH_2C_6H_5$ | O |
| 56 | F | Cl | 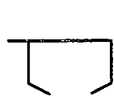 | $CF_2H$ | $CH_2OCH_3$ | O |
| 57 | F | Cl | 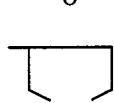 | $CF_2H$ | $CH_2SCH_3$ | O |
| 58 | F | Cl | 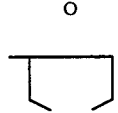 | $CF_2H$ | $C_2H_5$ | O |
| 59 | F | $CH_3$ | 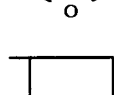 | $CF_2H$ | $CH_3$ | O |
| 60 | F | $CFH_2$ | 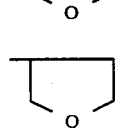 | $CF_2H$ | $CH_3$ | O |
| 61 | Cl | $CFH_2$ | 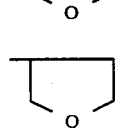 | $CF_2H$ | $CH_3$ | O |

TABLE 1-continued
Representative Compounds
| Cpd. No. | X$^1$ | X$^2$ | R | R$^1$ | R$^2$ | W |
|---|---|---|---|---|---|---|
| 62 | F | Cl |  | CF$_2$H | CH$_2$CN | O |
| 63 | F | Cl |  | CF$_2$H | CH$_3$ | O |
| 64 | F | Cl |  | CF$_2$H | CF$_2$H | O |
| 65 | F | Cl |  | CF$_2$H | CH$_2$CN | O |
| 66 | F | Cl |  | CF$_2$CHClF | CH$_3$ | O |
| 67 | F | Cl |  | CH$_2$CN | CH$_3$ | O |
| 68 | F | Cl |  | CH$_3$ | CH$_3$ | O |
| 69 | F | Cl |  | (CH$_2$)$_2$SCH$_3$ | CH$_3$ | O |
| 70 | F | Cl |  | CF$_2$H | CH$_3$ | S |
| 71 | F | Cl |  | CF$_2$H | CH$_3$ | S |
| 72 | Cl | Cl |  | CF$_2$H | CH$_3$ | S |
| 73 | F | Cl |  | (CH$_2$)$_2$S(O)CH$_3$ | CH$_3$ | O |
| 74 | F | Cl |  | (CH$_2$)$_2$S(O)CH$_3$ | CH$_3$ | S |

TABLE 1-continued
Representative Compounds

| Cpd. No. | X¹ | X² | R | R¹ | R² | W |
|---|---|---|---|---|---|---|
| 75 | F | Cl | tetrahydrofuran-2-yl | (CH$_2$)$_2$S(O)$_2$CH$_3$ | CH$_3$ | O |
| 76 | F | Cl | tetrahydrofuran-2-yl | CF$_2$H | CH$_2$S(O)CH$_3$ | O |
| 77 | F | Cl | tetrahydrofuran-2-yl | CF$_2$H | CH$_2$S(O)$_2$CH$_3$ | O |
| 78 | F | Cl | tetrahydrofuran-2-yl | (CH$_2$)$_2$OCH$_2$CH=CH$_2$ | CH$_3$ | O |
| 79 | F | Cl | tetrahydrofuran-2-yl | (CH$_2$)$_2$OCH$_2$C≡CH | CH$_3$ | O |
| 80 | Cl | Cl | CH$_2$-(tetrahydrofuran-2-yl) | CH$_2$CN | CH$_3$ | O |
| 81 | F | Cl | tetrahydrofuran-2-yl | CH$_2$CN | CF$_2$H | O |
| 82 | F | Cl | tetrahydrofuran-2-yl | CFH$_2$ | CF$_2$H | O |
| 83 | Cl | Cl | tetrahydrofuran-2-yl | CFH$_2$ | CH$_3$ | O |
| 84 | F | CFH$_2$ | tetrahydrofuran-2-yl | CH$_2$CN | CH$_3$ | O |
| 85 | Cl | Cl | tetrahydrofuran-2-yl | (CH$_2$)$_3$F | CH$_3$ | O |
| 86 | F | F | tetrahydrofuran-2-yl | (CH$_2$)$_3$F | CH$_3$ | O |
| 87 | F | Cl | tetrahydrofuran-2-yl | CF$_2$H | CFH$_2$ | O |

TABLE 1-continued

Representative Compounds

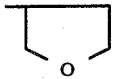

| Cpd. No. | $X^1$ | $X^2$ | R | $R^1$ | $R^2$ | W |
|---|---|---|---|---|---|---|
| 88 | F | Br | 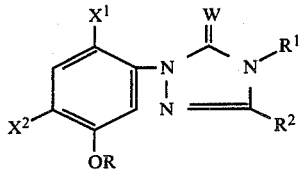 | $CF_2H$ | $CH_3$ | O |

Other representative compounds are those which are identical with compounds 1–37 and 39–87 respectively, except that $X^1$ is F and $X^2$ is Br. Still other representative compounds are those which are identical with compounds 1–87 respectively, except that $X^1$ is F and $X^2$ is $CF_3$. Other representative compounds are those which are identical with compounds 1–21, 24–28 and 31–87 respectively except that $X^1$ is Br.

EXAMPLE 1

1-[2,4-DICHLORO-5-(3-TETRAHYDROFURANYLOXY)PHENYL]-3-METHYL-4-DIFLUOROMETHYL-$\Delta^2$-1,2,4-TRIAZOLIN-5-ONE Step 1: 3-Tetrahydrofuran 4-methylphenylsulfonate A stirred solution of 10.0 g (0.11 mole) of 3-hydroxytetrahydrofuran in 36.0 g (0.46 mole) of pyridine was cooled in an ice bath and 22.0 g (0.12 mole) of 4-methylphenylsulfonyl chloride was added. Upon complete addition, the reaction mixture was stirred at ambient temperature for 60 hours. The reaction mixture was poured into ice-water, and the mixture extracted with diethyl ether. The combined ether extracts were washed several times with water. The organic layer was dried with magnesium sulfate, filtered, and the filtrate concentrated under reduced pressure to give 21.4 g of 3-tetrahydrofuranyl 4-methylphenylsulfonate.

The nmr spectrum was consistent with the proposed structure.

Step 2:
1-[2,4-Dichloro-5-(3-tetrahydrofuranyloxy)phenyl]-3-methyl-4-difluoromethyl-$\Delta^2$-1,2,4-triazolin-5-one To a stirred mixture of 1.0 g (0.003 mole) of 1-(2,4-dichloro-5-hydroxyphenyl)-3-methyl-4-difluoromethyl-$\Delta^2$-1,2,4-triazolin-5-one and 0.08 g (0.003 mole) of sodium hydride (0.16 g of 50% dispersion in mineral oil) in dimethylformamide was added 0.8 g (0.003 mole) of 3-tetrahydrofuranyl 4-methylphenylsulfonate. Upon complete addition, the reaction mixture was heated to reflux and stirred for 16 hours. The reaction mixture was concentrated under reduced pressure to give a residue which was dissolved in diethyl ether and washed with aqueous 10% sodium hydroxide. The organic layer was dried with magnesium sulfate, filtered, and the filtrate concentrated under reduced pressure to give a residual oil. The oil was stirred with petroleum ether until a solid formed. The solid was collected by filtration to give 0.78 g of 1-[2,4-dichloro-5-(3-tetrahydrofuranyloxy)phenyl]-3-methyl-4-difluoromethyl-$\Delta^2$-1,2,4-triazolin-5-one; mp 113°–116° C.

The nmr spectrum was consistent with the proposed structure.

EXAMPLE 2

1-(2,4-DICHLORO-5-TETRAHYDROFURFURYLOXYPHENYL)-3-METHYL-4-DIFLUOROMETHYL-$\Delta^2$-1,2,4-TRIAZOLIN-5-ONE A stirred mixture of 0.75 g (0.0024 mole) of 1-(2,4-dichloro-5-hydroxyphenyl)-3-methyl-4-difluoromethyl-$\Delta^2$-1,2,4-triazolin-5-one and 0.059 g (0.0024 mole) of sodium hydride (0.12 g of 50% dispersion in mineral oil) in 8 mL of dimethylformamide was warmed to 105° C. The mixture was cooled to 70° C., and 0.40 g (0.0024 mole) of tetrahydrofurfuryl bromide was added. Upon complete addition, the reaction mixture was heated at 75°–80° C. for 30 minutes, then allowed to cool to ambient temperature and was stirred for 16 hours. The reaction mixture was warmed to 125°–145° C. and stirred for 3.5 hours. An additional 3–4 drops of tetrahydrofurfuryl bromide was added, and the reaction mixture was stirred at 125°–145° C. for an additional 1.5 hours. The mixture was cooled and concentrated under reduced pressure to give a residual oil which was partitioned between diethyl ether and water. The ether layer was washed with water, aqueous 10% hydrochloric acid, water, aqueous 10% sodium hydroxide, and finally two portions of water. The organic layer was dried over magnesium sulfate, filtered, and the filtrate concentrated under reduced pressure to give a residual oil. The oil was stirred with cold petroleum ether until a solid formed. The solid was collected by filtration to give 0.25 g of 1-(2,4-dichloro-5-tetrahydrofurfuryloxyphenyl)-3-methyl-4-difluoromethyl-$\Delta^2$-1,2,4-triazolin-5-one. A sample was recrystallized from ethanol/water for analytical purposes; mp 95°–97.5° C.

The nmr spectrum was consistent with the proposed structure.

Analysis calcd for $C_{15}H_{15}Cl_2F_2N_3O_3$: C, 45.70; H, 3.84; N, 10.65; Found: C, 45.68; H, 4.05; N, 10.35.

EXAMPLE 3

1-(2,4-DICHLORO-5-TETRAHYDROFURFURYLOXYPHENYL)-3-METHYL-4-(2-PROPENYL)-$\Delta^2$-1,2,4-TRIAZOLIN-5-ONE In the manner of Example 1, treatment of 0.75 g (0.0025 mole) of 1-(2,4-dichloro-5-hydroxyphenyl)-3-methyl-4-(2-propenyl)-$\Delta^2$-1,2,4-triazolin-5-one with 0.41 g (0.0025 mole) of tetrahydrofurfuryl bromide in the presence of 0.06 g (0.0025 mole) of sodium hydride and dimethylformamide at room temperature for 16 hours, then at reflux for 2 hours gave 0.45 g of product as an oil.

The nmr spectrum was consistent with the proposed structure.

EXAMPLE 4

1-[2,4-DICHLORO-5-(TETRAHYDROPYRAN-2-YLMETHOXY)PHENYL]-3-METHYL-4-DIFLUOROMETHYL-$\Delta^2$-1,2,4-TRIAZOLIN-5-ONE A mixture of 1.0 g (0.0032 mole) of 1-(2,4-dichloro-5-hydroxyphenyl)-3-methyl-4-difluoromethyl-$\Delta^2$-1,2,4-triazolin-5-one and 0.078 g (0.0033 mole) of sodium hydride in 12 mL of dimethylformamide was heated to reflux, then cooled to room temperature. Tetrahydropyran-2-ylmethyl bromide (0.58 g, 0.0032 mole) was added dropwise over one minute, and the reaction mixture was heated with stirring at reflux temperature for 2 hours. The mixture was allowed to cool to room temperature and was stirred for about 64 hours, then heated again at reflux temperature for 2 hours. An additional 0.2 g (0.0011 mole) of tetrahydropyran-2-ylmethyl bromide was added and refluxing was resumed for an additional 2 hours.

The reaction mixture was cooled and concentrated to dryness to give an oily black residue which was partitioned between diethyl ether and water. The ether layer was washed sequentially with 10% hydrochloric acid, water, 10% aqueous solution of sodium hydroxide, water, and brine. The ether layer was dried over magnesium sulfate, filtered, and the filtrate concentrated to give 0.82 g of a viscous yellow oil. The oil crystallized upon treatment with petroleum ether to give 0.46 g of product, mp 101°–102° C.

The nmr spectrum was consistent with the proposed structure.

Analysis calcd for $C_{16}H_{17}Cl_2F_2N_3O_3$: C, 47.08; H, 4.20; N, 10.30; Found: C, 46.79; H, 4.13; N, 10.39.

EXAMPLE 5

1-[2,4-DICHLORO-5-(TETRAHYDROPYRAN-2-YLMETHOXY)PHENYL]-3-METHYL-4-(2-PROPENYL)-$\Delta^2$-1,2,4-TRIAZOLINE-5-ONE in the manner of Example 4, 0.89 g (0.005 mole) of tetrahydropyran-2-ylmethyl bromide was added at room temperature to a perviously heated then cooled mixture of 1.5 g (0.005 mole) of 1-(2,4-dichloro-5-hydroxyphenyl)-3-methyl-4-(2-propenyl)-$\Delta^2$-1,2,4-triazolin-5-one and 0.13 g (0.0055 mole) of sodium hydride in 10 mL of dimethylformamide. The mixture was stirred at reflux temperature for 1.5 hours, then at room temperature for 16 hours, and finally at reflux temperature for an additional 2 hours. The mixture was diluted with water, extracted with diethyl ether, and the ether layer treated as in Example 4 to give 0.81 g of product as an oil.

The nmr spectrum was consistent with the proposed structure.

EXAMPLE 6

1-[2,4-DICHLORO-5-(1,3-DIOXOLAN-2-YLMETHOXY)PHENYL]-3-METHYL-4-DIFLUOROMETHYL-$\Delta^2$-1,2,4-TRIAZOLIN-5-ONE In the manner of Example 4, 0.44 g (0.0026 mole) of 1,3-dioxolan-2-ylmethyl bromide was added to a previously heated (110° C.) then cooled (25° C.) mixture of 0.75 g (0.0024 mole) of 1-(2,4-dichloro-5-hydroxyphenyl)-3-methyl-4-difluoromethyl-$\Delta^2$-1,2,4-triazolin-5-one and 0.07 g (0.0029 mole) of sodium hydride in dimethylformamide, and the mixture was heated at reflux temperature for 3 hours to give 0.62 g of product, mp 117°–123° C.

The nmr spectrum was consistent with the proposed structure.

EXAMPLE 7

1-{2,4-DICHLORO-5-[2-(1,3-DIOXOLAN-2-YL)ETHOXY]PHENYL}-3-METHYL-4-DIFLUOROMETHYL-$\Delta^2$-1,2,4-TRIAZOLIN-5-ONE In the manner of Example 4, treatment of 0.75 g (0.0024 mole) of 1-(2,4-dichloro-5-hydroxyphenyl)-3-methyl-4-difluoromethyl-$\Delta^2$-1,2,4-triazolin-5-one with 0.44 g (0.0026 mole) of 2-(1,3-dioxolan-2-yl)ethyl bromide in the presence of 0.065 g (0.0027 mole) of sodium hydride and dimethylformamide at reflux temperature for 3 hours gave 0.6 g of product, mp 106°–109° C.

The nmr spectrum was consistent with the proposed structure.

Analysis calcd for $C_{15}H_{15}Cl_2F_2N_3O_4$: C, 43.92; H, 3.69; N, 10.24; Found: C, 46.29; H, 4.18; N, 9.66.

EXAMPLE 8

1-[2,4-DICHLORO-5-(2,2-DIMETHYL-1,3-DIOXOLAN-4-YLMETHOXY)PHENYL]-3-METHYL-4-DIFLUOROMETHYL-$\Delta^2$-1,2,4-TRIAZOLIN-5-ONE In the manner of Example 4, 0.687 g (0.0024 mole) of 2,2-dimethyl-1,3-dioxolan-4-ylmethyl 4-methylphenylsulfonate was added to a mixture of 0.75 g (0.0024 mole) of 1-(2,4-dichloro-5-hydroxyphenyl)-3-methyl-4-difluoromethyl-$\Delta^2$-1,2,4-triazolin-5-one and 0.072 g (0.003 mole) of sodium hydride in 8 mL of dimethylformamide and the whole was heated to about 120° C. over about 2 hours to give 0.4 g of semi-solid product.

The nmr spectrum was consistent with the proposed structure.

EXAMPLE 9

1-{2,4-DICHLORO-5-[3-(2-METHYL-1,3-DIOXOLAN-2-YL)PROPOXY]PHENYL}-3-METHYL-4-DIFLUOROMETHYL-$\Delta^2$-1,2,4-TRIAZOLIN-5-ONE In the manner of Example 4, the reaction of 0.9 g (0.003 mole) of 1-(2,4-dichloro-5-hydroxyphenyl)-3-methyl-4-difluoromethyl-$\Delta^2$-1,2,4-triazolin-5-one with 0.07 g (0.003 mole) of sodium hydride and 0.48 g (0.003 mole) of 3-(2-methyl-1,3-dioxolan-2-yl)propyl chloride in the presence of dimethylformamide gave 0.86 g of product, mp 109°–111° C.

The nmr spectrum was consistent with the proposed structure.

EXAMPLE 10

1-(2,4-DICHLORO-5-FURFURYLOXYPHENYL)-3-METHYL-4-DIFLUOROMETHYL-$\Delta^2$-1,2,4-TRIAZOLIN-5-ONE Furfuryl bromide was prepared by the method of Example 21 of U.S. Pat. No. 4,282,219 as follows. A stirred solution of 2.0 g (0.02 mole) of furfuryl alcohol in 20 mL of diethyl ether was cooled to 5° C., and a solution of 2.0 g (0.007 mole) of phosphorus tribromide in 6 mL of diethyl ether was added dropwise over 30 minutes. Upon complete addition, the reaction mixture was stirred an additional 15 minutes at 5° C. The clear diethyl ether solution was then decanted from a dark residue. The clear solution was stirred at 5°-6° C. with 0.5 g of anhydrous potassium carbonate for 10 minutes. The solution was decanted away from the potassium carbonate and kept cold. The unstable product, furfuryl bromide, was used as such without delay in the following reaction.

To a slurry of 1.55 g (0.005 mole) 1-(2,4-dichloro-5-hydroxyphenyl)-3-methyl-4-difluoromethyl-$\Delta^2$-1,2,4-triazolin-5-one and 0.48 g (0.0035 mole) of potassium carbonate in 25 mL of acetone, previously cooled to about 8°-9° C., was added portion-wise over about 0.5 hour about 10 mL of the solution of crude furfuryl bromide in diethyl ether prepared above. The reaction mixture was heated to about 40° C. over 3-5 hours, then the remainder of the ether solution of furfuryl bromide was added and heating at about 40° C. was continued for about 16 hours. The reaction mixture was filtered, and the filtrate washed sequentially with water, 10% hydrochloric acid, water, twice with a 10% aqueous solution of sodium hydroxide, and twice with water. The organic layer was dried over magnesium sulfate, filtered, and the filtrate concentrated to give 1.6 g of a dark oily-solid residue. The residue crystallized upon treatment with petroleum ether, wgt. 0.91 g, mp 134°-135° C. A sample for analysis was prepared by recrystallization from ethanol, m.p. 135°-137° C.

The nmr spectrum was consistent with the proposed structure.

Analysis calcd for $C_{15}H_{11}Cl_2F_2N_3O_3$: C, 46.17; H, 2.84; N, 10.77; Found: C, 46.11; H, 2.74; N, 10.11.

EXAMPLE 11

1-[2,4-DICHLORO-5-(2-THIENYLMETHOXY)-PHENYL]-3-METHYL-4-DIFLUOROMETHYL-$\Delta^2$-1,2,4-TRIAZOLIN-5-ONE In the manner of Example 1, the reaction of 0.75 g (0.0024 mole) of 1-(2,4-dichloro-5-hydroxyphenyl)-3-methyl-4-difluoromethyl-$\Delta^2$-1,2,4-triazolin-5-one, 0.42 g (0.0024 mole) of 2-thenyl bromide, and 0.1 g (0.004 mole) of sodium hydride in 20 mL of dimethylformamide gave 0.53 g of product, mp 154°-155° C.

The nmr spectrum was consistent with the proposed structure.

Analysis calcd for $C_{15}H_{11}Cl_2F_2N_3O_3$: C, 44.35; H, 2.73; N, 10.34; Found: C, 44.36; H, 2.81; N, 10.02.

EXAMPLE 12

1-[2,4-DICHLORO-5-(1,3-DIOXAN-4-YLMETHOXY)PHENYL]-3-METHYL-4-DIFLUOROMETHYL-$\Delta^2$-1,2,4-TRIAZOLIN-5-ONE In the manner of Example 4, the addition of 0.68 g (0.005 mole) of 1,3-dioxan-4-ylmethyl chloride to a previously heated then cooled mixture of 0.75 g (0.0025 mole) of 1-(2,4-dichloro-5-hydroxyphenyl)-3-methyl-4-difluoromethyl-$\Delta^2$-1,2,4-triazolin-5-one and 0.072 g (0.003 mole) of sodium hydride in dimethylformamide gave, after heating at reflux for about 2 hours, 0.2 g of product as an oil.

The nmr spectrum was consistent with the proposed structure.

EXAMPLE 13

1-[2,4-DICHLORO-5-(1,4-BENZODIOXAN-2-YLMETHOXY)PHENYL]-3-METHYL-4-DIFLUOROMETHYL-$\Delta^2$-1,2,4-TRIAZOLIN-5-ONE To a solution of 5 g (0.03 mole) of 1,4-benzodioxan-2-methanol in 125 mL of pyridine was added at 0° C. 6.29 g (0.033 mole) of 4-methylphenylsulfonyl chloride, and the mixture was stirred for 3 hours. The reaction mixture was poured into ice water, and the whole was extracted with chloroform. The chloroform layer was dried over magnesium sulfate, filtered, and the filtrate concentrated to give an oily residue which solidified when stirred with water. The solid product, 1,4-benzodioxan-2-ylmethyl 4-methylphenylsulfonate, was collected on a filter paper and air dried, mp 73°-75° C.

In the manner of Example 4, a mixture of 0.5 g (0.0017 mole) of 1-(2,4-dichloro-5-hydroxyphenyl)-3-methyl-4-difluoromethyl-$\Delta^2$-1,2,4-triazolin-5-one and 0.045 g (0.0019 mole) of sodium hydride in 10 mL of dimethylformamide was stirred at room temperature for 20 minutes; 0.54 g (0.0017 mole) of 1,4-benzodioxan-2-ylmethyl 4-methylphenylsulfonate was added and the mixture stirred first at room temperature for 1 hour then at 100° C. for 2 hours to give 0.33 g of product as an oil.

The nmr spectrum was consistent with the proposed structure.

EXAMPLE 14

1-[2,4-DICHLORO-5-(TETRAHYDRO-4H-PYRAN-4-YLOXY)PHENYL]-3-METHYL-4-DIFLUOROMETHYL-$\Delta^2$-1,2,4-TRIAZOLIN-5-ONE To a chilled solution of 1.0 g (0.0098 mole) of tetrahydro-4H-pyran-4-ol in 10 mL of pyridine was added 1.91 g (0.01 mole) of 4-methylphenylsulfonyl chloride over 3-5 minutes. The reaction mixture was stirred at about −4° C. for 15 minutes, then was allowed to stand with cooling for 16 hours. The reaction mixture was mixed with ice-water, and the solid product, tetrahydro-4H-pyran-4-yl 4-methylphenylsulfonate, collected on a filter paper, wgt. 1.6 g, mp 56°-57° C.

In the manner of Example 4, 0.615 g (0.0024 mole) of tetrahydro-4H-pyran-4-yl 4-methylphenylsulfonate was added to a previously heated (60° C.) then cooled (25° C.) mixture of 0.75 g (0.0024 mole) of 1-(2,4-dichloro-5-hydroxyphenyl)-3-methyl-4-difluoromethyl-$\Delta^2$-1,2,4-triazolin-5-one and 0.065 g (0.0027 mole) of sodium hydride in 8 mL of dimethylformamide, and the mixture was heated at about 90° C. for 16 hours to give 0.42 g of product, mp 149°-151° C.

The nmr spectrum was consistent with the proposed structure.

EXAMPLE 15

1-[2,4-DICHLORO-5-(5,6-DIHYDRO-2H-PYRAN-3-YLMETHOXY)PHENYL]-3-METHYL-4-DIFLUOROMETHYL-$\Delta^2$-1,2,4-TRIAZOLIN-5-ONE Step 1: 5,6-Dihydro-3-hydroxymethyl-2H-pyran This compound was prepared by the reduction of 14 g (0.125 mole) of 5,6-dihydro-2H-pyran-3-carbaldehyde with 2.88 g (0.074 mole) of sodium borohydride in a 1:1 mixture of dioxane and water; wgt. 15 g.

Step 2: 5,6-Dihydro-3-chloromethyl-2H-pyran

Reaction of 5 g (0.0438 mole) of 5,6-dihydro-3-hydroxymethyl-2H-pyran with 11.51 g (0.0448 mole) of triphenyl phosphine in the presence of 20 mL of carbon tetrachloride at room temperature for about 40 hours produced this intermediate as a solid material.

Step 3: 1-[2,4-Dichloro-5-(5,6-dihydro-2H-pyran-3-ylmethoxy)phenyl]-3-methyl-4-difluoromethyl-$\Delta^2$-1,2,4-triazolin-5-one In the manner of Example 4, 0.3 g (0.0023 mole) of 5,6-dihydro-3-chloromethyl-2H-pyran was added dropwise to a previously heated (75° C.) then cooled (25° C.) mixture of 0.7 g (0.0023 mole) of 1-(2,4-dichloro-5-hydroxyphenyl)-3-methyl-4-difluoromethyl-$\Delta^2$-1,2,4-triazolin-5-one and 0.055 g (0.0023 mole) of sodium hydride in 25 mL of dimethylformamide, and the mixture was heated to 90° C. for 2 hours then stirred at room temperature for 16 hours and finally heated at 110° C. for 1.5 hours to give 0.49 g of product, mp 143°–144° C.

The nmr spectrum was consistent with the proposed structure.

EXAMPLE 16

1-[2,4-DICHLORO-5-(1,3-DIOXOLAN-2-YLMETHOXY)PHENYL]-3-METHYL-4-(2-PROPENYL)-$\Delta^2$-1,2,4-TRIAZOLIN-5-ONE In the manner of Example 4, 0.44 g (0.0026 mole) of 1,3-dioxolan-2-ylmethyl bromide was added to a previously heated (90° C.) then cooled (25° C.) mixture of 0.75 g (0.0025 mole) of 1-(2,4-dichloro-5-hydroxyphenyl)-3-methyl-4-(2-propenyl)-$\Delta^2$-1,2,4-triazolin-5-one and 0.07 g (0.0029 mole) of sodium hydride in 10 mL of dimethylformamide, and the mixture was heated at reflux for 2.5 hours to give 0.45 g of product as a waxy solid.

The nmr spectrum was consistent with the proposed structure.

EXAMPLE 17

1-[2,4-DICHLORO-5-(3-TETRAHYDROFURANYLOXY)PHENYL]-3-METHYL-4-(2-PROPENYL)-$\Delta^2$-1,2,4-TRIAZOLIN-5-ONE In the manner of Example 4, 0.61 g (0.0025 mole) of 3-tetrahydrofuranyl 4-methylphenylsulfonate was added to a mixture of 0.75 g (0.0025 mole) of 1-(2,4-dichloro-5-hydroxyphenyl)-3-methyl-4-(2-propenyl)-$\Delta^2$-1,2,4-triazolin-5-one and 0.06 g (0.0025 mole) of sodium hydride in 30 mL of dimethylformamide, and the mixture was heated at reflux temperatures for 3 hours then stirred at room temperature for about 64 hours to give 0.7 g of a solid product. An nmr analysis of the product showed the reaction had not gone to completion. The crude product was dissolved in a small amount of diethyl ether, the solution filtered to remove insoluble impurities, and the filtrate concentrated to give 0.4 g of a solid residue. The 0.4 g residue was treated with an additional 0.012 g (0.0005 mole) of sodium hydride and 0.15 g (0.0005 mole) of 5-hydroxyphenyl compound in dimethylformamide, and the mixture was heated at reflux temperature for 4 hours then stirred at room temperature for 16 hours to give 0.36 g of desired product as an oil.

The nmr spectrum was consistent with the proposed structure.

EXAMPLE 18

1-[2,4-DICHLORO-5-(3-TETRAHYDROFURANYLOXY)PHENYL]-3-METHYL-4-n-PROPYL-$\Delta^2$-1,2,4-TRIAZOLIN-5-ONE In the manner of Example 4, 0.80 g (0.0033 mole) of 3-tetrahydrofuranyl 4-methylphenylsulfonate was added to a mixture of 1.0 g (0.0033 mole) of 1-(2,4-dichloro-5-hydroxyphenyl)-3-methyl-4-n-propyl-$\Delta^2$-1,2,4-triazolin-5-one and 0.08 g (0.0033 mole) of sodium hydride in dimethylformamide, and the mixture was heated at 80°–90° C. for 2 hours, at reflux temperature for 6.5 hours, then stirred at room temperature for 16 hours and finally heated at reflux temperature for an additional 5 hours to give 1.0 g of product as an oil which solidified upon standing, mp 107°–112° C. A sample of the product was recrystallized from ethyl acetate-hexane for analytical purposes, m.p. 116°–117° C.

The nmr spectrum was consistent with the proposed structure.

Analysis calcd for $C_{16}H_{19}Cl_2N_3O_3$: C, 51.63; H, 5.14; N, 11.29; Found: C, 51.55; H, 5.11; N, 11.02.

EXAMPLE 19

1-(2,4-DICHLORO-5-TETRAHYDROFURFURYLOXYPHENYL)-3-METHYL-4-n-PROPYL-$\Delta^2$-1,2,4-TRIAZOLIN-5-ONE In the manner of Example 4, 0.49 g (0.003 mole) of tetrahydrofurfuryl bromide was added to a mixture of 0.90 g (0.003 mole) of 1-(2,4-dichloro-5-hydroxyphenyl)-3-methyl-4-n-propyl-$\Delta^2$-1,2,4-triazolin-5-one and 0.075 g (0.0031 mole) of sodium hydride in dimethylformamide, and the mixture was heated at 80° C. for 45 minutes, then stirred at room temperature for 16 hours, and again heated (90°–100° C.) for 1 hour. Analysis (TLC) of the reaction mixture showed the reaction to be incomplete. Powdered potassium carbonate (0.21 g, 0.0015 mole) and an additional 0.49 g (0.003 mole) of tetrahydrofurfuryl bromide were added, and the reaction mixture was heated at 90°–100° C. for 2.5 hours, stirred at room temperature for 16 hours, heated at reflux temperature for 6.5 hours, stirred at room temperature for 16 hours, and, finally, heated at reflux for 5 hours to give 0.97 g of product as a viscous oil.

The nmr spectrum was consistent with the proposed structure.

EXAMPLE 20

1-[2,4-DICHLORO-5-(2,2-DIMETHYL-1,3-DITHIOLAN-4-YLMETHOXY)PHENYL]-3-METHYL-4-DIFLUOROMETHYL-$\Delta^2$-1,2,4-TRIAZOLIN-5-ONE Step 1: 2,2-Dimethyl-4-hydroxymethyl-1,3-dithiolan To a mixture of 10.18 g (0.082 mole) of 2,3-dimercapto-1-propanol, 20 mL of cyclohexane, and 5.0 g (0.086 mole) of acetone was added 4 drops of concentrated hydrochloric acid, and the mixture was stirred at reflux temperature for 3.5 hours to give, after fractional distillation of the reaction mixture, 5.85 g of a colorless oil, bp 96°–106° C./1.2–1.5 mm Hg, which solidified on standing. Recrystallization from toluene-hexane gave 3.96 g of product, mp 45°–50° C.

Step 2: 4-Chloromethyl-2,2-dimethyl-1,3-dithiolan

To a solution of 3.46 g (0.021 mole) of 2,2-dimethyl-4-hydroxymethyl-1,3-dithiolan in 15 mL of toluene was added dropwise 2.35 g (0.020 mole) of thionyl chloride, and the mixture was heated gradually to 80°–85° C., maintained at that temperature for 0.75 hour, then stirred at room temperature for 16 hours. The mixture was filtered, and the filtrate concentrated to dryness at 60° C./100 mm Hg to give a residual oil. Distillation of the oil gave 1.81 g of product, bp 75°–78° C./1.25–1.35 mm Hg.

Step 3: 1-[2,4-Dichloro-5-(2,2-dimethyl-1,3-dithiolan-4-ylmethoxy)phenyl]-3-methyl-4-difluoromethyl-$\Delta^2$-1,2,4-triazolin-5-one In the manner of Example 4, 0.493 g (0.0027 mole) of 4-chloromethyl-2,2-dimethyl-1,3-dithiolan was added to a previously heated (65° C.) then cooled (25° C.) mixture of 0.75 g (0.0024 mole) of 1-(2,4-dichloro-5-hydroxyphenyl)-3-methyl-4-difluoromethyl-$\Delta^2$-1,2,4-triazolin-5-one and 0.072 g (0.003 mole) of sodium hydride in 8 mL of dimethylformamide, and the mixture was heated over 3.5 hours to about 100° C. to give 0.9 g of product as a waxy solid. Crystallization in the presence of petroleum ether gave 0.5 g of crystalline product, mp 108°–110° C.

The nmr spectrum was consistent with the proposed structure.

Analysis calcd for $C_{16}H_{17}Cl_2F_2N_3O_2S_2$: C, 42.11; H, 3.76; N, 9.21; Found: C, 41.89; H, 3.62; N, 9.05.

EXAMPLE 21

1-[2,4-DICHLORO-5-(TETRAHYDRO-4H-THIOPYRAN-4-YLOXY)PHENYL]-3-METHYL-4-DIFLUOROMETHYL-$\Delta^2$-1,2,4-TRIAZOLIN-5-ONE Step 1: Tetrahydro-4H-thiopyran-4-ol To a stirred solution of 0.8 g (0.021 mole) of sodium borohydride in 30 mL of 1:1 dioxane-water was added a solution of 5.0 g (0.043 mole) of tetrahydro-4H-thiopyran-4-one in 20 mL of dioxane, and the solution was stirred at room temperature for 16 hours. The reaction mixture was concentrated to give a residue which was dissolved in chloroform and washed with water. Concentration of the chloroform solution gave 4.5 g of product as an oil which solidified upon standing.

Step 2: Tetrahydro-4H-thiopyran-4-yl 4-methylphenylsulfonate

To a solution of 4.1 g (0.015 mole) of tetrahydro-4H-thiopyran-4-ol in 40 mL of pyridine, cooled in an ice bath, was added 2.90 g (0.15 mole) of 4-methylphenylsulfonyl chloride, and the reaction mixture was stirred at room temperature for 16 hours. The mixture was poured into a mixture of ice and water, and the whole extracted with diethyl ether. The organic phase was washed with water then with a 10% aqueous solution of sodium hydroxide, dried, and concentrated to give 5.8 g of product as an oil.

Step 3: 1-[2,4-Dichloro-5-(tetrahydro-4H-thiopyran-4-yloxy)phenyl]-3-methyl-4-difluoromethyl-$\Delta^2$-1,2,4-triazolin-5-one In the manner of Example 4, the reaction of 0.75 g (0.0024 mole) of 1-(2,4-dichloro-5-hydroxyphenyl)-3-methyl-4-difluoromethyl-$\Delta^2$-1,2,4-triazolin-5-one, 0.06 g (0.0025 mole) of sodium hydride, and 0.66 g (0.0024 mole) of tetrahydro-4H-thiopyran-4-yl 4-methylphenylsulfonate in dimethylformamide gave 0.4 g of product as a waxy solid.

The nmr spectrum was consistent with the proposed structure.

EXAMPLE 22

1-[2,4-DIBROMO-5-(3-TETRAHYDROFURANYLOXY)PHENYL]-3-METHYL-4-DIFLUOROMETHYL-$\Delta^2$-1,2,4-TRIAZOLIN-5-ONE Step 1: 3-Methoxyphenyl hydrazine A stirred solution of 50.0 g (0.41 mole) of 3-methoxyaniline in 60 mL of concentrated sulfuric acid and 100 mL of water was cooled to −5° C., and a solution of 28.0 g (0.41 mole) of sodium nitrite in water was added slowly while maintaining the temperature of the reaction mixture below 0° C. The mixture was stirred at 0° C. for 1 hour, then added slowly to a chilled, stirred solution of 100 g (0.44 mole) of stannous chloride dihydrate in 300 mL of concentrated hydrochloric acid. After complete addition, the reaction mixture was allowed to warm to ambient temperature and stand for 16 hours. The reaction mixture was filtered and the filter cake made basic and extracted with diethyl ether. The reaction mixture filtrate was also made basic and extracted with diethyl ether. The ether extracts were combined and dried with magnesium sulfate. The mixture was filtered and the filtrate concentrated under reduced pressure to give 49.1 g of product as an oil.

The nmr spectrum was consistent with the proposed structure.

Step 2: Pyruvic acid, 3-methoxyphenyl hydrazone.

To a stirred solution of 45 g (0.33 mole) of 3-methoxyphenyl hydrazine in 400 mL aqueous 1N hydrochloric acid and 400 mL of ethanol was added dropwise a solution of 31.5 g (0.36 mole) of pyruvic acid in 30 mL of water. After complete addition, the reaction mixture was stirred at ambient temperature for 3 hours, and 200 mL of water was added. The mixture was filtered to give 56 g of product; mp 113°–114° C.

The nmr spectrum was consistent with the proposed structure.

Step 3:
1-(3-Methoxyphenyl)-3-methyl-Δ²-1,2,4-triazolin-5-one

To a stirred mixture of 55.5 g (0.27 mole) of pyruvic acid, 3-methoxyphenyl hydrazone in 1500 mL of toluene was added 27.0 g (0.27 mole) of triethylamine. The mixture was warmed until a clear solution formed. Diphenyl phosphoryl azide, 64.8 g (0.27 mole) was added at 35° C., and the reaction mixture was warmed to 75° C. and stirred until evolution of nitrogen stopped. The reaction mixture was heated to reflux temperature and stirred for 16 hours. The mixture was extracted with aqueous 10% sodium hydroxide. The extract was washed with toluene and acidified. The resultant solid was collected by filtration and air dried to give 36.0 g of product; mp 143°–146° C.

The nmr spectrum was consistent with the proposed structure.

Step 4:
1-(3-Methoxyphenyl)-3-methyl-4-difluoromethyl-Δ²-1,2,4-triazolin-5-one To a stirred solution of 31.0 g (0.15 mole) of 1-(3-methoxyphenyl)-3-methyl-Δ²-1,2,4-triazolin-5-one, 31.0 g (0.10 mole) of tetrabutylammonium bromide, 31.0 g (0.77 mole) of sodium hydroxide in 1500 mL of cyclohexane was added 62.0 g (0.72 mole) of gaseous chlorodifluoromethane. The addition caused the reaction mixture to reflux. After complete addition, the reaction mixture was cooled. The supernatant liquid was decanted and washed sequentially with aqueous 10% hydrochloric acid, water, and aqueous 10% sodium hydroxide. The organic layer was dried with magnesium sulfate and filtered. The filtrate was concentrated under reduced pressure to give 28.0 g of product as a solid.

The nmr spectrum was consistent with the proposed structure.

Step 5:
1-(2,4-Dibromo-5-methoxyphenyl)-3-methyl-4-difluoromethyl-Δ²-1,2,4-triazolin-5-one To a stirred solution of 12.0 g (0.047 mole) of 1-(3-methoxyphenyl)-3-methyl-4-difluoromethyl-Δ²-1,2,4-triazolin-5-one in 75 mL of acetic acid was added dropwise 30.0 g (0.18 mole) of bromine. Upon complete addition, the reaction mixture was heated at reflux for 6 hours. The reaction mixture was concentrated under reduced pressure. The residue was dissolved in diethyl ether and washed with aqueous 10% sodium thiosulfate and water. The organic layer was dried with magnesium sulfate and filtered. The filtrate was concentrated under reduced pressure to give 17.4 g of product as a solid.

The nmr spectrum was consistent with the proposed structure.

Analysis calcd for $C_{11}H_9Br_2F_2N_3O_2$: C, 32.00; H, 2.20; N, 10.17; Found: C, 31.21; H, 1.81; N, 9.28.

Step 6:
1-(2,4-Dibromo-5-hydroxyphenyl)-3-methyl-4-difluoromethyl-Δ²-1,2,4-triazolin-5-one A solution of 17.2 g (0.042 mole) of 1-(2,4-dibromo-5-methoxyphenyl)-3-methyl-4-difluoromethyl-Δ²-1,2,4-triazolin-5-one in 100 mL of methylene chloride was added dropwise with stirring to 50.6 g (0.20 mole) of boron tribromide in methylene chloride. Upon complete addition, the reaction mixture was stirred at ambient temperature for 18 hours. The reaction mixture was washed with 50 mL of water. The organic layer was separated, dried with magnesium sulfate, and filtered. The filtrate was concentrated under reduced pressure to give 16.1 g of product; mp 137°–140° C.

The nmr spectrum was consistent with the proposed structure.

Step 7:
1-[2,4-Dibromo-5-(3-tetrahydrofuranyloxy)phenyl]-3-methyl-4-difluoromethyl-Δ²-1,2,4-trizaolin-5-one In the manner of Example 4, the reaction of 1.0 g (0.0025 mole) of 1-(2,4-dibromo-5-hydroxyphenyl)-3-methyl-4-difluoromethyl-Δ²-1,2,4-triazolin-5-one (which may be prepared as described in steps 1–6 above), 0.06 g (0.0025 mole) of sodium hydride, and 0.61 g (0.0025 mole) of 3-tetrahydrofuranyl 4-methylphenylsulfonate (which may be prepared as described in Example 1, step 1) in dimethylformamide gave 0.95 g of crude product as a solid material. Treatment with petroleum ether gave 0.83 g of crystalline product, mp 138°–140° C.

The nmr spectrum was consistent with the proposed structure.

Analysis calcd for $C_{14}H_{13}Br_2F_2N_3O_3$: C, 35.85; H, 2.79; N, 8.96; Found: C, 36.87; H, 3.08; N, 9.13.

EXAMPLE 23

1-(2,4-DIBROMO-5-TETRAHYDROFURFURYLOXYPHENYL)-3-METHYL-4-DIFLUOROMETHYL-Δ²-1,2,4-TRIAZOLIN-5-ONE

In the manner of Example 4, the reaction of 1.0 g (0.0025 mole) of 1-(2,4-dibromo-5-hydroxyphenyl)-3-methyl-4-difluoromethyl-Δ²-1,2,4-triazolin-5-one (see Example 22, step 6), 0.06 g (0.0025 mole) of sodium hydride, and 0.41 g (0.0025 mole) of tetrahydrofurfuryl bromide in dimethylformamide gave 0.8 g of product as an oil.

The nmr spectrum was consistent with the proposed structure.

EXAMPLE 24

1-[2,4-DICHLORO-5-(3-TETRAHYDROTHIENYLOXY)PHENYL]-3-METHYL-4-DIFLUOROMETHYL-Δ²-1,2,4-TRIAZOLIN-5-ONE

Step 1: 3-Tetrahydrothienyl 4-methylphenylsulfonate

To a chilled solution of 1.12 g (0.0098 mole) of tetrahydrothiophene-3-ol in 15 mL of pyridine was added 1.91 g (0.01 mole) of 4-methylphenylsulfonyl chloride, and the reaction mixture was stirred in the cold, about 16° C., for 1 hour then placed in a cold refrigerator for 16 hours. The reaction mixture was allowed to warm to room temperature and was stirred for 1 hour. An additional 0.3 g (0.0016 mole) of 4-methylphenylsulfonyl chloride was added, and the reaction mixture was stirred at room temperature for 64 hours. The reaction mixture was poured into water, and the whole was extracted with methylene chloride. The methylene chloride solution was dried and concentrated to give 1.28 g of product as an oil.

The nmr spectrum was consistent with the proposed structure.

Step 2:
1-[2,4-Dichloro-5-(3-tetrahydrothienyloxy)phenyl]-3-methyl-4-difluoromethyl-Δ²-1,2,4-triazolin-5-one In the manner of Example 4, 0.644 g (0.0024 mole) of 3-tetrahydrothienyl 4-methylphenylsulfonate was added to a previously heated (110° C.) then cooled (25° C.) mixture of 0.75 g (0.0024 mole) 1-(2,4-dichloro-5-hydroxyphenyl)-3-methyl-4-difluoromethyl-Δ²-1,2,4-triazolin-5-one and 0.065 g (0.0027 mole) of sodium hydride in 10 mL of dimethylformamide, and the mixture was heated over 1.5 hours to 85° C., then over 3.5 hours to 135° C. to give 0.58 g of product, mp 136°–140° C.

The nmr spectrum was consistent with the proposed structure.

Analysis calcd for $C_{14}H_{13}Cl_2F_2N_3O_2S$: C, 42.44; H, 3.31; N, 10.60; Found: C, 43.87; H, 3.72; N, 10.08.

EXAMPLE 25
1-[2,4-DICHLORO-5-(1-OXO-3-TETRAHYDROTHIENYLOXY)PHENYL]-3-METHYL-4-DIFLUOROMETHYL-Δ²-1,2,4-TRIAZOLIN-5-ONE

To a solution of 0.25 g (0.00063 mole) of 1-[2,4-dichloro-5-(3-tetrahydrothienyloxy)phenyl]-3-methyl-4-difluoromethyl-Δ²-1,2,4-triazolin-5-one (Example 24) in 4 mL of glacial acetic acid was added 0.06 mL (0.0007 mole) of a 30% aqueous solution of hydrogen peroxide, and the reaction mixture was stirred at room temperature for 16 hours. The reaction mixture was concentrated to a moist solid residue which upon treatment with water gave 0.16 g of desired product, mp 183°–186° C.

The nmr spectrum was consistent with the proposed structure.

Analysis calcd for $C_{14}H_{13}Cl_2F_2N_3O_3S$: C, 40.79; H, 3.18; N, 10.19; Found: C, 41.77; H, 3.50; N, 9.68.

EXAMPLE 26
1-[2,4-DICHLORO-5-(1,1-DIOXO-3-TETRAHYDROTHIENYLOXY)PHENYL]-3-METHYL-4-DIFLUOROMETHYL-Δ²-1,2,4-TRIAZOLIN-5-ONE

A mixture of 0.1 g (0.00025 mole) of 1-[2,4-dichloro-5-(3-tetrahydrothienyloxy)phenyl]-3-methyl-4-difluoromethyl-Δ²-1,2,4-triazolin-5-one (Example 24), 0.10 mL (0.00116 mole) of a 30% aqueous solution of hydrogen peroxide, and 2 mL of glacial acetic acid was heated at 56° C. for 3 hours. The reaction mixture was concentrated to a waxy solid which upon treatment with water gave 0.06 g of product, mp 201°–203° C.

Elemental and nmr analyses were conducted on samples of the same product produced in a second run of this reaction.

The nmr spectrum was consistent with the proposed structure.

Analysis calcd for $C_{14}H_{13}Cl_2F_2N_3O_4S$: C, 39.27; H, 3.06; N, 9.81; Found: C, 39.16; H, 3.18; N, 9.66.

EXAMPLE 27
1-[2,4-DICHLORO-5-(2,2-DIMETHYL-1,1,3,3-TETRAOXO-1,3-DITHIOLAN-4-YLMETHOXY)PHENYL]-3-METHYL-4-DIFLUOROMETHYL-Δ²-1,2,4-TRIAZOLIN-5-ONE

To a solution of 0.18 g (0.0004 mole) of 1-[2,4-dichloro-5-(2,2-dimethyl-1,3-dithiolan-4-ylmethoxy)phenyl]-3-methyl-4-difluoromethyl-Δ²-1,2,4-triazolin-5-one (Example 20) in 4 mL of glacial acetic acid was added 0.15 mL (0.0017 mole) of a 30% aqueous solution of hydrogen peroxide, and the reaction mixture was stirred at room temperature for 15 minutes, then heated at reflux for 15 minutes, and finally stirred again at room temperature for 16 hours. An additional 0.10 mL (0.0012 mole) of 30% hydrogen peroxide solution was added, and the reaction mixtue was heated to reflux for about 1 hour. The reaction mixture was diluted with water and the product was collected on a filter paper, 0.21 g, mp >184° C. (cloudy).

The nmr spectrum was consistent with the proposed structure.

Analysis calcd for $C_{16}H_{17}Cl_2F_2N_3O_6S_2$: C, 36.93; H, 3.29; N, 8.08; Found: C, 35.38; H, 3.24; N, 7.54.

EXAMPLE 28
1-[2-CHLORO-4-METHYL-5-(TETRAHYDRO-4H-THIOPYRAN-4-YLOXY)PHENYL]-3-METHYL-4-DIFLUOROMETHYL-Δ²-1,2,4-TRIAZOLIN-5-ONE

Step 1: 4-Methyl-3-methoxyphenyl hydrazine.

The compound was prepared by a method analogous to that of Example 22, Step 1. The reaction of 100 g (0.73 mole) of 4-methyl-3-methoxyaniline and 50.5 g (0.73 mole) of sodium nitrite in the presence of 330 g (1.46 moles) of stannous chloride dihydrate, 1160 mL of concentrated hydrochloric acid and 250 mL of water gave 58.0 g of product as an oil.

The nmr spectrum was consistent with the proposed structure.

Step 2: Pyruvic acid, 4-methyl-3-methoxyphenyl hydrazone.

This compound was prepared by a method analogous to that of Example 22, Step 2. The reaction of 57.6 g (0.378 mole) of 4-methyl-3-methoxyphenyl hydrazine and 33.3 g (0.378 mole) of pyruvic acid in the presence of 400 mL of 1N hydrochloric acid and 400 mL of ethanol gave 59.0 g of product as a solid.

The nmr spectrum was consistent with the proposed structure.

Step 3: 1-(4-Methyl-3-methoxyphenyl)-3-methyl-Δ²-1,2,4-triazolin-5-one.

This compound was prepared by a method analogous to that of Example 22, Step 3. The reaction of 56.8 g (0.256 mole) of pyruvic acid, 4-methyl-3-methoxyphenyl hydrazone and 70.3 g (0.256 mole) of diphenyl phosphoryl azide in the presence of 25.9 g (0.256 mole) of triethylamine in 1500 mL of toluene gave 75.0 g of damp product; mp 165°–168° C.

The nmr spectrum was consistent with the proposed structure.

Step 4: 1-(4-Methyl-3-methoxyphenyl)-3-methyl-4-difluoromethyl-Δ²-1,2,4-triazolin-5-one.

This compound was prepared by a method analogous to that of Example 22, Step 4. The reaction of 60.0 g (0.276 mole) of 1-(4-methyl-3-methoxyphenyl)-3-methyl-Δ²-1,2,4-triazolin-5-one and 60.0 g (0.67 mole) of chlorodifluoromethane in the presence of 60.0 g (1.5 moles) of sodium hydroxide and 60.0 g (0.186 mole)

tetrabutylammonium bromide in 2000 mL of cyclohexane gave 18.5 g of product as a solid.

The nmr spectrum was consistent with the proposed structure.

Step 5:
1-(2-Chloro-4-methyl-5-methoxyphenyl)-3-methyl-4-difluoromethyl-$\Delta^2$-1,2,4-triazolin-5-one.

A solution of 15.0 g (0.056 mole) of 1-(4-methyl-3-methoxyphenyl)-3-methyl-4-difluoromethyl-$\Delta^2$-1,2,4-triazolin-5-one and 7.5 g (0.056 mole) of sulfuryl chloride in 100 mL of chloroform was stirred at ambient temperature for 2 hours. The reaction mixture was concentrated under reduced pressure to give a residue. The residue was dissolved in methylene chloride and washed with aqueous 10% sodium hydroxide. The organic layer was dried with magnesium sulfate and filtered. The filtrate was concentrated under reduced pressure to give 16.5 g of product as a solid.

The nmr spectrum was consistent with the proposed structure.

Step 6:
1-(2-Chloro-4-methyl-5-hydroxyphenyl)-3-methyl-4-difluoromethyl-$\Delta^2$-1,2,4-triazolin-5-one.

This compound was prepared by a method analogous to that of Example 22, Step 6. The reaction of 16.0 g (0.053 mole) of 1-(2-chloro-4-methyl-5-methoxyphenyl)-3-methyl-4-difluoromethyl-$\Delta^2$-1,2,4-triazolin-5-one and 39.6 g (0.158 mole) of boron tribromide in 100 mL of methylene chloride gave 10.5 g of product as a solid.

The nmr spectrum was consistent with the proposed structure.

Step 7:
1-[2-Chloro-4-methyl-5-(tetrahydro-4H-thiopyran-4-yloxy)phenyl]-3-methyl-4-difluoromethyl-$\Delta^2$-1,2,4-triazolin-5-one.

In the manner of Example 4, the reaction of 0.66 g (0.0023 mole) of 1-(2-chloro-4-methyl-5-hydroxyphenyl)-3-methyl-4-difluoromethyl-$\Delta^2$-1,2,4-triazolin-5-one (which may be prepared as described in steps 1–6 above), 0.055 g (0.0023 mole) of sodium hydride, and 0.55 g (0.0020 mole) of tetrahydro-4H-thiopyran-4-yl 4-methylphenylsulfonate in 25 mL of dimethylformamide gave 0.75 g of product as an oil.

The nmr spectrum was consistent with the proposed structure.

EXAMPLE 29

1-[2,4-DIBROMO-5-(1-METHYL-3-PYRROLIDINYLOXY)PHENYL]-3-METHYL-4-DIFLUOROMETHYL-$\Delta^2$-1,2,4-TRIAZOLIN-5-ONE Step 1: 1-Methyl-3-pyrrolidinyl 4-methylphenylsulfonate To a mixture of 3.0 g (0.03 mole) of 3-hydroxy-1-methylpyrrolidine, 3.1 g (0.03 mole) of triethylamine, and 25 mL of methylene chloride was added 5.6 g (0.03 mole) of 4-methylphenylsulfonyl chloride, and the reaction mixture was stirred at room temperature for 3 hours. The reaction mixture was concentrated to a residue. The residue was dissolved in ether, the solution filtered, and the filtrate concentrated to give 5.75 g of product as an oil.

The nmr spectrum was consistent with the proposed structure.

Step 2:
1-[2,4-Dibromo-5-(1-methyl-3-pyrrolidinyloxy)phenyl]-3-methyl-4-difluoromethyl-$\Delta^2$-1,2,4-triazolin-5-one In the manner of Example 4, the reaction of 0.75 g (0.0019 mole) of 1-(2,4-dibromo-5-hydroxyphenyl)-3-methyl-4-difluoromethyl-$\Delta^2$-1,2,4-triazolin-5-one (Example 22, step 6), 0.05 g (0.0019 mole) of sodium hydride, and 0.48 g (0.0019 mole) of 1-methyl-3-pyrrolidinyl 4-methylphenylsulfonate in 25 mL of dimethylformamide gave 0.58 g of product as an oil.

The nmr spectrum was consistent with the proposed structure.

EXAMPLE 30

1-[2-BROMO-4-METHYL-5-(3-TETRAHYDROFURANYLOXY)PHENYL]-3-METHYL-4-DIFLUOROMETHYL-$\Delta^2$-1,2,4-TRIAZOLIN-5-ONE Step 1:
1-(2-Bromo-4-methyl-5-methoxyphenyl)-3-methyl-4-difluoromethyl-$\Delta^2$-1,2,4-triazolin-5-one A solution of 2.0 g (0.007 mole) of 1-(4-methyl-3-methoxyphenyl)-3-methyl-4-difluoromethyl-$\Delta^2$-1,2,4-triazolin-5-one (which may be prepared as described in Example 28, step 4) and 1.5 g (0.009 mole) of bromine in 50 mL of acetic acid was stirred at ambient temperature for 18 hours. The acetic acid was removed under reduced pressure, and the residue dissolved in methylene chloride. The solution was washed with aqueous 10% sodium bisulfate. The organic layer was dried with magnesium sulfate and filtered. The filtrate was concentrated under reduced pressure to give 2.4 g of product as a solid; mp 132°–134° C.

The nmr spectrum was consistent with the proposed structure.

Step 2:
1-(2-Bromo-4-methyl-5-hydroxyphenyl)-3-methyl-4-difluoromethyl-$\Delta^2$-1,2,4-triazolin-5-one To a stirred solution of 2.1 g (0.006 mole) of 1-(2-bromo-4-methyl-5-methoxyphenyl)-3-methyl-4-difluoromethyl-$\Delta^2$-1,2,4-triazolin-5-one in 30 mL of methylene chlorine at ambient temperature was added 4.4 g (0.018 mole) of boron tribromide. Upon complete addition, the reaction mixture was stirred at ambient temperature for 18 hours. Water, 25 mL, was stirred into the reaction mixture. The layers were separated, and the organic layer dried with magnesium sulfate. The mixture was filtered, and the filtrate concentrated to give 1.5 g of product, mp 143°–144° C.

The nmr spectrum was consistent with the proposed structure.

Step 3:
1-[2-Bromo-4-methyl-5-(3-tetrahydrofuranyloxy)-phenyl]-3-methyl-4-difluoromethyl-$\Delta^2$-1,2,4-triazolin-5-one In the manner of Example 4, the reaction of 0.5 g (0.0015 mole) of 1-(2-bromo-4-methyl-5-hydroxyphenyl)-3-methyl-4-difluoromethyl-$\Delta^2$-1,2,4-triazolin-5-one, 0.036 g (0.0015 mole) of sodium hydride, and 0.36 g (0.0015 mole) of 3-tetrahydrofuranyl 4-methylphenylsulfonate (which may be prepared as described in Example 1, step 1) in 20 mL of dimethylformamide gave 0.46 g of product as an oil.

The nmr spectrum was consistent with the proposed structure.

EXAMPLE 31

1-[2,4-DICHLORO-5-(1-METHYL-3-PYRROLIDINYLOXY)PHENYL]-3-METHYL-4-DIFLUOROMETHYL-$\Delta^2$-1,2,4-TRIAZOLIN-5-ONE In the manner of Example 4, the reaction of 0.75 g (0.0019 mole) of 1-(2,4-dichloro-5-hydroxyphenyl)-3-methyl-4-difluoromethyl-$\Delta^2$-1,2,4-triazolin-5-one, 0.046 g (0.0019 mole) of sodium hydride, and 0.49 g (0.0019 mole) of 1-methyl-3-pyrrolidinyl 4-methylphenylsulfonate (Example 29, step 1) in 30 mL of dimethylformamide gave 0.4 g of product as an oil.

The nmr spectrum was consistent with the proposed structure.

EXAMPLE 32

1-[2-CHLORO-4-METHYL-5-(3-TETRAHYDROFURANYLOXY)PHENYL]-3-METHYL-4-DIFLUOROMETHYL-$\Delta^2$-1,2,4-TRIAZOLIN-5-ONE In the manner of Example 4, the reaction of 0.8 g (0.0028 mole) of 1-(2-chloro-4-methyl-5-hydroxyphenyl)-3-methyl-4-difluoromethyl-$\Delta^2$-1,2,4-triazolin-5-one (which may be prepared as described in Example 28, steps 1-6), 0.07 g (0.0029 mole) of sodium hydride, and 0.67 g (0.0028 mole) of 3-tetrahydrofuranyl 4-methylphenylsulfonate (which may be prepared as described in Example 1, step 1) in dimethylformamide gave 0.75 g of product as an oil.

The nmr spectrum was consistent with the proposed structure.

EXAMPLE 33

1-(2-CHLORO-4-METHYL-5-TETRAHYDROFURFURYLOXYPHENYL)-3-METHYL-4-DIFLUOROMETHYL-$\Delta^2$-1,2,4-TRIAZOLIN-5-ONE In the manner of Example 4, the reaction of 0.8 g (0.0028 mole) of 1-(2-chloro-4-methyl-5-hydroxyphenyl)-3-methyl-4-difluoromethyl-$\Delta^2$-1,2,4-triazolin-5-one (which may be prepared as described in Example 28, steps 1-6), 0.07 g (0.0029 mole) of sodium hydride, and 0.46 g (0.0028 mole) of tetrahydrofurfuryl bromide in dimethylformamide gave 0.47 g of product as an oil.

The nmr spectrum was consistent with the proposed structure.

EXAMPLE 34

1-[2,4-DICHLORO-5-(1,1-DIOXOTETRAHYDRO-4H-THIOPYRAN-4-YLOXY)PHENYL]-3-METHYL-4-DIFLUOROMETHYL-$\Delta^2$-1,2,4-TRIAZOLIN-5-ONE A mixture of 0.34 g (0.00083 mole) of 1-[2,4-dichloro-5-(tetrahydro-4H-thiopyran-4-yloxy)phenyl]-3-methyl-4-difluoromethyl-$\Delta^2$-1,2,4-triazolin-5-one (Example 21), 10 mL (0.116 mole) of a 30% aqueous solution of hydrogen peroxide, and 25 mL of glacial acetic acid was heated at reflux temperature for 3 hours. The reaction mixture was concentrated to a residue. The residue was dissolved in methylene chloride and washed with a 10% aqueous solution of sodium hydroxide. The methylene chloride layer was dried and concentrated to give 0.25 g of product as an oil.

The nmr spectrum was consistent with the proposed structure.

EXAMPLE 35

1-[2,4-DICHLORO-5-(3-TETRAHYDROFURANYLOXY)PHENYL]-3-CHLORO-4-(2-PROPENYL)-$\Delta^2$-1,2,4-TRIAZOLIN-5-ONE In the manner of Example 4, the reaction of 1.8 g (0.0056 mole) of 1-(2,4-dichloro-5-hydroxyphenyl)-3-chloro-4-(2-propenyl)-$\Delta^2$-1,2,4-triazolin-5-one, 0.15 g (0.0062 mole) of sodium hydride, and 1.49 g (0.0062 mole) of 3-tetrahydrofuranyl 4-methylphenylsulfonate (which may be prepared as described in Example 1, step 1) in 11 mL of dimethylformamide gave, after recrystallization from heptane-ethyl acetate, 1.1 g of product, mp 137°-138° C.

The nmr spectrum was consistent with the proposed structure.

EXAMPLE 36

1-[2,4-DICHLORO-5-(3-TETRAHYDROFURANYLOXY)PHENYL]-3-ETHYL-4-DIFLUOROMETHYL-$\Delta^2$-1,2,4-TRIAZOLIN-5-ONE This compound was prepared by a method similar to that of Example 1. The reaction of 0.63 g (0.0019 mole) of 1-(2,4-dichloro-5-hydroxyphenyl)-3-ethyl-4-difluoromethyl-$\Delta^2$-1,2,4-triazolin-5-one with 0.47 g (0.0019 mole) of 3-tetrahydrofuranyl 4-methylphenylsulfonate, in the presence of 0.048 g (0.002 mole) of sodium hydride and 5 mL of dimethylformamide gave 0.57 g of product mp 115°-118° C.

The nmr spectrum was consistent with the proposed structure.

The intermediate 1-(2,4-dichloro-5-hydroxyphenyl)-3-ethyl-4-difluoromethyl-$\Delta^2$-1,2,4-triazolin-5-one may be prepared by a method similar to that of Example 38 (steps 1-6) below starting with 2,4-dichlorophenol and proceeding via the intermediates 2,4-dichloro-5-(1-methylethoxy)aniline (step 1), 2,4-dichloro-5-(1-methylethoxy)phenylhydrazine (step 2), 2-ketobutyric acid 2,4-dichloro-5-(1-methylethoxy)phenylhydrazone (step 3) -use 2-ketobutyric acid rather than pyruvic acid, 1-[2,4-dichloro-5-(1-methylethoxy)phenyl]-3-ethyl-$\Delta^2$-1,2,4-triazolin-5-one (step 4), and 1-[2,4-dichloro-5-(1-methylethoxy)phenyl]-3-ethyl-4-difluoromethyl-$\Delta^2$-1,2,4-triazolin-5-one.

EXAMPLE 37

1-[2,4-DICHLORO-5-(3-TETRAHYDROFURANYLOXY)PHENYL]-3-(2,2-DIMETHYLPROPYL)-4-DIFLUOROMETHYL-$\Delta^2$-1,2,4-TRIAZOLIN-5-ONE Step 1:
1-(3-Methoxyphenyl)-3-(1,1-dimethylethyl)-$\Delta^2$-1,2,4-triazolin-5-one 3-Methoxyphenylhydrazine, prepared from 10.0 g (0.0573 mole) of the hydrochloride salt by treatment with potassium carbonate in the presence of water and xylene, was reacted with 10.4 g (0.06 mole) of ethyl pivaloylcarbamate in the presence of 1.5 g of phosphorus pentoxide in xylene to give 3.84 g of product.

The nmr spectrum was consistent with the proposed structure.

Step 2:
1-(3-Methoxyphenyl)-3-(1,1-dimethylethyl)-4-difluoromethyl-$\Delta^2$-1,2,4-triazolin-5-one The reaction of 3.87 g (0.01565 mole) of 1-(3-methoxyphenyl)-3-(1,1-dimethylethyl)-$\Delta^2$-1,2,4-triazolin-5-one with an excess of chlorodifluoromethane in the presence of 4 g of sodium hydroxide, 4 g of tetrabutylammonium bromide, 220 mL of cyclohexane, and 10 mL of tetrahydrofuran gave 3.64 g of product as an oil.

The nmr spectrum was consistent with the proposed structure.

Step 3:
1-(2,4-Dichloro-5-methoxyphenyl)-3-(1,1-dimethylethyl)-4-difluoromethyl-$\Delta^2$-1,2,4-triazolin-5-one The 3-methoxyphenyl product from step 2 (3.21 g, 0.0108 mole) was treated with 10 mL of sulfuryl chloride to give 2.83 g of the 2,4-dichloro-5-methoxyphenyl product, mp 129°-132° C.

The nmr spectrum was consistent with the proposed structure.

Step 4:
1-(2,4-Dichloro-5-hydroxyphenyl)-3-(1,1-dimethylethyl)-4-difluoromethyl-$\Delta^2$-1,2,4-triazolin-5-one Treatment of 2.47 g (0.00675 mole) of 1-(2,4-dichloro-5-methoxyphenyl)-3-(1,1-dimethylethyl)-4-difluoromethyl-$\Delta^2$-1,2,4-triazolin-5-one with 20 mL of a 1.0 molar solution of boron tribromide in methylene chloride (0.0202 mole of BBr$_3$) gave 2.02 g of product, mp 133°-136° C.

The nmr spectrum was consistent with the proposed structure.

Step 5:
1-[2,4-Dichloro-5-(3-tetrahydrofuranyloxy)phenyl]-3-(1,1-dimethylethyl)-4-difluoromethyl-$\Delta^2$-1,2,4-triazolin-5-one This compound was prepared by a method similar to that of Example 1. The reaction of 0.5 g (0.0014 mole) of 1-(2,4-dichloro-5-hydroxyphenyl)-3-(1,1-dimethylethyl)-4-difluoromethyl-$\Delta^2$-1,2,4-triazolin-5-one with 0.34 g (0.0014 mole) of 3-tetrahydrofuranyl 4-methylphenylsulfonate in the presence of 0.036 g (0.0015 mole) of sodium hydride and 5 mL of dimethylformamide gave 0.42 g of product as an oil.

The nmr spectrum was consistent with the proposed structure.

EXAMPLE 38

1-[4-CHLORO-2-FLUORO-5-(3-TETRAHYDROFURANYLOXY)PHENYL]-3-METHYL-4-DIFLUOROMETHYL-$\Delta^2$-1,2,4-TRIAZOLIN-5-ONE

Step 1: 4-Chloro-2-fluoro-5-methoxyaniline

The intermediate 4-chloro-2-fluoro-5-methoxyaniline was prepared in a five step synthesis from commercially available 2-chloro-4-fluorophenol as detailed by E. Nagano, et al. in European Patent Application No. 69,855, incorporated herein by reference.

Step 2: 4-Chloro-2-fluoro-5-methoxyphenylhydrazine

A stirred solution of 48.0 g (0.27 mole) of 4-chloro-2-fluoro-5-methoxyaniline in 500 mL of concentrated hydrochloric acid was cooled to −5° C. and 23.5 g (0.34 mole) of sodium nitrite in 100 mL of water was added dropwise. After complete addition, the reaction mixture was stirred at 0° C. for one hour. A second solution of 154.0 g (0.68 mole) of stannous chloride in 225 mL of concentrated hydrochloric acid was cooled to 0° C., and the cold diazonium solution prepared above was added to it slowly. After complete addition, the reaction mixture was allowed to warm to ambient temperature. The reaction mixture was filtered to collect a solid. This solid was dissolved in an aqueous 50% sodium hydroxide solution, and the solution extracted with toluene. The toluene extract was dried with magnesium sulfate and filtered. The filtrate was concentrated under reduced pressure to yield 22.4 g of 4-chloro-2-fluoro-5-methoxyphenylhydrazine as a solid.

The nmr spectrum was consistent with the proposed structure.

Step 3: Pyruvic acid, 4-chloro-2-fluoro-5-methoxyphenylhydrazone

A stirred solution of 21.0 g (0.11 mole) of 4-chloro-2-fluoro-5-methoxyphenylhydrazine and 100 mL of aqueous 10% hydrochloric acid in 100 mL of ethanol was warmed to 40° C., and a solution of 10.0 g (0.114 mole) of pyruvic acid in 20 mL of water was added. Upon complete addition, the reaction mixture was stirred for one hour. An additional 50 mL of water was added and the reaction mixture filtered to collect a solid. The solid was air dried to yield 29.0 g of pyruvic acid, 4-chloro-2-fluoro-5-methoxyphenylhydrazone; mp 166°-196° C.

The nmr spectrum was consistent with the proposed structure.

Step 4:
1-(4-Chloro-2-fluoro-5-methoxyphenyl)-3-methyl-$\Delta^2$-1,2,4-triazolin-5-one A stirred solution of 27.0 g (0.104 mole) of pyruvic acid, 4-chloro-2-fluoro-5-methoxyphenylhydrazone, 29.0 g (0.105 mole) of diphenyl phosphoryl azide, and 11.0 g (0.108 mole) of triethylamine in 500 mL of toluene was heated under reflux for four hours. The reaction mixture was cooled to ambient temperature and extracted with an aqueous 10% sodium hydroxide solution. The extract was neutralized with gaseous carbon dioxide, and a solid was collected by filtration. The solid was air dried to yield 11.0 g of 1-(4-chloro-2-fluoro-5-methoxyphenyl)-3-methyl-$\Delta^2$-1,2,4-triazolin-5-one, mp 193°-195° C.

The nmr spectrum was consistent with the proposed structure.

Step 5:
1-(4-Chloro-2-fluoro-5-methoxyphenyl-3-methyl-4-difluoromethyl-$\Delta^2$-1,2,4-triazolin-5-one A stirred mixture of 10.0 g (0.039 mole) of 1-(4-chloro-2-fluoro-5-methoxyphenyl)-3-methyl-$\Delta^2$-1,2,4-triazolin-5-one, 10.0 g (0.031 mole) of tetrabutylammonium bromide and 10.0 g (0.25 mole) of sodium hydroxide in 250 mL of cyclohexane was warmed to 60° C. Chlorodifluoromethane, 10.0 g (0.12 mole) was bubbled into the reaction mixture. After complete addition, the reaction mixture was warmed to reflux and stirred for one hour. The hot solution was decanted from a pot residue and cooled to ambient temperature. Methylene chloride was added to the cooled mixture to dissolve a solid precipitate. The mixture was washed with 10% hydrochloric acid, then with an aqueous 10% sodium hydroxide solution. The organic layer was dried with anhydrous magnesium sulfate and filtered. The filtrate was concentrated under reduced pressure to yield 5.0 g of 1-(4-chloro-2-fluoro-5-methoxyphenyl)-3-methyl-4-difluoromethyl-Δ²-1,2,4-triazolin-5-one; mp 86°–88° C.

The nmr spectrum was consistent with the proposed structure.

Step 6:
1-(4-Chloro-2-fluoro-5-hydroxyphenyl)-3-methyl-4-difluoromethyl-Δ²-1,2,4-triazolin-5-one A stirred solution of 4.6 g (0.015 mole) of 1-(4-chloro-2-fluoro-5-methoxyphenyl)-3-methyl-4-difluoromethyl-Δ²-1,2,4-triazolin-5-one in 200 mL of methylene chloride was cooled to 10° C., and a solution of 11.2 g (0.045 mole) of boron tribromide in 45 mL of methylene chloride was added. Upon complete addition, the reaction mixture was stirred for four hours as it warmed to ambient temperature. After this time 100 mL of water was added, and the reaction mixture continued to stir for an additional 18 hours. The organic layer was separated, dried with anhydrous magnesium sulfate, and filtered. The filtrate was concentrated under reduced pressure to yield 4.4 g of 1-(4-chloro-2-fluoro-5-hydroxyphenyl)-4-difluoromethyl-3-methyl-Δ²-1,2,4-triazolin-5-one; mp 147°–152° C.

The nmr spectrum was consistent with the proposed structure.

Step 7:
1-[4-Chloro-2-fluoro-5-(3-tetrahydrofuranyloxy)-phenyl]-3-methyl-4-difluoromethyl-Δ²-1,2,4-triazolin-5-one This compound was prepared by the method similar to that of Example 1. The reaction of 0.7 g (0.00238 mole) of 1-(4-chloro-2-fluoro-5-hydroxyphenyl)-3-methyl-4-difluoromethyl-Δ²-1,2,4-triazolin-5-one (which may be prepared as described in steps 1–6 above) with 0.6 g (0.00247 mole) of 3-tetrahydrofuranyl 4-methylphenylsulfonate in the presence of 0.06 g (0.00247 mole) of sodium hydride and 30 mL of dimethylformamide gave 0.54 g of product as an oil.

The nmr spectrum was consistent with the proposed structure.

EXAMPLE 39

1-(4-CHLORO-2-FLUORO-5-TETRAHYDROFUR-FURYLOXYPHENYL)-3-METHYL-4-DIFLUOROMETHYL-Δ²-1,2,4-TRIAZOLIN-5-ONE

This compound was prepared by the reaction of 0.7 g (0.00238 mole) of 1-(4-chloro-2-fluoro-5-hydroxyphenyl)-3-methyl-4-difluoromethyl-Δ²-1,2,4-triazolin-5-one with 0.4 g (0.00242 mole) of tetrahydrofurfuryl bromide in the presence of 0.06 g (0.00247 mole) of sodium hydride and 30 mL of dimethylformamide; yield, 0.25 g as an oil.

The nmr spectrum was consistent with the proposed structure.

HERBICIDAL ACTIVITY

The test species used in demonstrating the herbicidal activity of compounds of this invention include cotton (*Gossypium hirsutum* var. Stoneville), soybean (*Glycine max* var. Williams), field corn (*Zea mays* var. Agway 595S), rice (*Oryza sativa* var. Labelle), wheat (*Triticum aestivium* var. Prodax), field bindweed (*Convolvulus arvensis*), morningglory (*Ipomea lacunosa* or *Ipomea hederacea*), velvetleaf (*Abutilon theophrasti*), barnyardgrass (*Echinochola crus* galli), green foxtail (*Setaria viridis*), johnsongrass (*Sorghum halepense*), and yellow nutsedge (*Cyperus esculentus*).

Procedure:

Two disposable fiber flats (8 cm×15 cm×25 cm) for each rate of application for each candidate herbicide for preemergence testing were filled to an approximate depth of 6.5 cm with steam sterilized sandy loam soil. The soil was leveled and impressed with a template to provide six evenly spaced furrows 13 cm long and 0.5 cm deep in each flat. Seeds or tubers of cotton, soybean, corn, rice, wheat, and yellow nutsedge were planted in the furrows of the first flat, and seeds of bindweed, morningglory, velvetleaf, barnyardgrass, green foxtail, and johnsongrass were planted in the furrows of the second flat. The six-row template was again employed to firmly press the seeds or tubers into place. A topping soil of equal portions of sand and sandy loam soil was placed uniformly on top of each flat to a depth of approximately 0.5 cm. Flats for postemergence testing were prepared in the same manner.

The flats for the preemergence test were first watered, then drenched with a solution of test compound as described below. The flats were placed in a greenhouse and watered regularly at the soil surface for 21 days at which time phytotoxicity data were recorded.

The flats for the postemergence test were placed in a greenhouse and watered for 8–10 days, then the foliage of the emerged test plants was sprayed with a solution of the test compound. After spraying, the foliage was kept dry for 24 hours, then watered regularly for 21 days, and phytotoxicity data recorded.

In both preemergence and postemergence tests, the candidate herbicides were applied as aqueous-acetone solutions at rates equivalent to 8.0 kilograms/hectare (kg/ha) and submultiples thereof, i.e., 4.0 kg/ha, 2.0 kg/ha, and so on. Preemergence applications were made as soil drenches using 100 mL of test solution of appropriate concentration for each of the two flats/-compound. Postemergence applications were made as foliage sprays using 5 mL of test solution for each of the two flats.

For flats of the size described above, an application rate of 8.0 kg/ha of test compound is equivalent to 0.025 g/flat. A stock solution of 0.2 g of test compound in 40 mL of acetone containing 0.5% v/v of sorbitan monolaurate emulsifier/solubilizer was prepared. For the 8.0 kg/ha preemergence test, 10 mL of the stock solution was diluted with water to give 200 mL of test solution for application as a soil drench to both flats for the compound, 100 mL/flat. For the 8.0 kg/ha postemergence test, 10 mL of the stock solution was used undiluted as a spray, 5 mL/flat. The remaining 20 mL of stock solution was diluted with an equal volume of acetone-emulsifier to give 40 mL of a second stock solution, containing 0.1 g of test compound, and the process above repeated, i.e., 20 mL of the solution being used for the 4.0 kg/ha application rate, and 20 mL for the preparation of lower rate test solutions by the same process.

Herbicidal data at selected application rates are given for various compounds of the invention in the tables below. The test compounds are identified in the tables below by numbers which correspond to those in Table 1 above.

TABLE 2

Preemergence Herbicidal Activity [4.000 kg/ha]

| Species | Compound No % Kill at 4.000 kg/ha | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Cotton | 100 | 50 | 0 | 70 | 20 | 100 | 90 | 70 | 30 | 0 | 0 | 20 | 0 | 90 | 0 | 20 | 60 | 70 |
| Soybean | 100 | 0 | 100 | 60 | 50 | 100 | 100 | 100 | 0 | 0 | 0 | 100 | 0 | 100 | 60 | 60 | 100 | 100 |
| Field Corn | 100 | 100 | 100 | 100 | 60 | 100 | 100 | 100 | 30 | 0 | 30 | 100 | 0 | 100 | 100 | 100 | 100 | 100 |
| Rice | 100 | 100 | 80 | 100 | 0 | 100 | 70 | 70 | 40 | 20 | 0 | 100 | 0 | 100 | 100 | 90 | 90 | 90 |
| Wheat | 100 | 100 | 100 | 100 | 100 | 100 | 100 | 100 | 80 | 40 | 20 | 100 | 0 | 100 | 100 | 100 | 100 | 100 |
| Field Bindweed | 100 | 100 | 100 | 100 | 100 | 100 | 100 | 100 | 100 | 100 | 0 | 100 | 90 | 100 | 100 | 50 | 80 | 70 |
| Morningglory | 100 | 100 | 100 | 90 | 100 | 100 | 100 | 100 | 90 | 70 | 40 | 90 | 0 | 100 | 90 | 60 | 95 | 90 |
| Velvetleaf | 100 | 100 | 100 | 100 | 100 | 100 | 100 | 100 | 100 | 100 | 100 | 100 | 100 | 100 | 100 | 100 | 100 | 100 |
| Barnyardgrass | 100 | 100 | 100 | 100 | 90 | 100 | 100 | 100 | 100 | 90 | 100 | 100 | 0 | 100 | 100 | 100 | 100 | 100 |
| Green Foxtail | 100 | 100 | 100 | 100 | 100 | 100 | 100 | 100 | 100 | 100 | 100 | 100 | 100 | 100 | 100 | 100 | 100 | 100 |
| Johnsongrass | 100 | 100 | 100 | 100 | 100 | 100 | 100 | 100 | 100 | 100 | 100 | 100 | 0 | 100 | 100 | 100 | 100 | 100 |
| Yellow Nutsedge | 100 | 60 | 0 | 0 | 0 | 90 | 70 | 20 | 0 | 0 | 0 | 30 | 0 | 100 | 20 | 0 | 95 | 80 |

| Species | Compound No % Kill at 4.000 kg/ha | | | | | | | | | | | | | | | | |
|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 |
| Cotton | 0 | 60 | 100 | 60 | 0 | 100 | 100 | 100 | 0 | 0 | 0 | 80 | 0 | 30 | 0 | 0 | 0 |
| Soybean | 0 | 80 | 100 | 100 | 0 | 100 | 100 | 100 | 0 | 0 | 0 | 0 | 0 | 60 | 60 | 50 | 100 |
| Field Corn | 90 | 60 | 100 | 100 | 100 | 100 | 100 | 100 | 0 | 100 | 0 | 100 | 100 | 100 | 100 | 30 | 30 |
| Rice | 20 | 0 | 100 | 100 | 40 | 100 | 100 | 100 | 0 | 10 | 0 | 100 | 100 | 100 | 80 | 0 | 100 |
| Wheat | 100 | 100 | 100 | 100 | 95 | 100 | 100 | 100 | 0 | 0 | 0 | 100 | 100 | 100 | 100 | 100 | 100 |
| Field Bindweed | 0 | 100 | 100 | 80 | 0 | 100 | 100 | 100 | 0 | 70 | 0 | 100 | 80 | 100 | 20 | 0 | 80 |
| Morningglory | 20 | 100 | 100 | 90 | 0 | 100 | 100 | 100 | 0 | 0 | 0 | 60 | 20 | 100 | 90 | 0 | 100 |
| Velvetleaf | 100 | 100 | 100 | 100 | 100 | 100 | 100 | 100 | 100 | 100 | 0 | 100 | 100 | 100 | 100 | 90 | 100 |
| Barnyardgrass | 50 | 100 | 100 | 100 | 100 | 100 | 100 | 100 | 0 | 90 | 40 | 100 | 100 | 100 | 100 | 0 | 100 |
| Green Foxtail | 90 | 100 | 100 | 100 | 100 | 100 | 100 | 100 | 100 | 100 | 95 | 100 | 100 | 100 | 100 | 95 | 100 |
| Johnsongrass | 30 | 100 | 100 | 100 | 100 | 100 | 100 | 100 | 0 | 90 | 50 | 100 | 100 | 100 | 100 | 30 | 100 |
| Yellow Nutsedge | 0 | 0 | 100 | 80 | 0 | 100 | 100 | 100 | 0 | 0 | 0 | 90 | 0 | 100 | 0 | 0 | 50 |

TABLE 3

Preemergence Herbicidal Activity [0.250 kg/ha]

| Species | Compound No % Kill at 0.250 kg/ha | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Cotton | 30 | 0 | 0 | 0 | 0 | 0 | 0 | 0 | 0 | 0 | 0 | 0 | 0 | 0 | 0 | 0 | 0 | 0 |
| Soybean | 30 | 0 | 0 | 0 | 0 | 0 | 0 | 0 | 0 | 0 | 0 | 0 | 0 | 0 | 0 | 0 | 0 | 0 |
| Field Corn | 100 | 100 | 0 | 35 | 0 | 0 | 80 | 95 | 30 | 0 | 0 | 30 | 0 | 100 | 60 | 0 | 70 | 30 |
| Rice | 90 | 0 | — | 20 | 0 | 60 | 10 | 0 | 0 | 0 | 0 | 30 | 0 | 95 | 50 | 0 | 20 | 0 |
| Wheat | 100 | 10 | — | 30 | 0 | 80 | 40 | 20 | 0 | 30 | 0 | 50 | 0 | 100 | 90 | 0 | 95 | 90 |
| Field Bindweed | 20 | 90 | 0 | 0 | 0 | 0 | 0 | 10 | 0 | 0 | 0 | 0 | 0 | 0 | 0 | 0 | 0 | 0 |
| Morningglory | 60 | 40 | 0 | 0 | 0 | 0 | 0 | 20 | 0 | 0 | 0 | 0 | 0 | 0 | 0 | 0 | 0 | 0 |
| Velvetleaf | 100 | 100 | 20 | 100 | 80 | 100 | 100 | 100 | 50 | 80 | 10 | 100 | 0 | 90 | 30 | 0 | 90 | 100 |
| Barnyardgrass | 100 | 100 | 0 | 100 | 0 | 70 | 100 | 80 | 0 | 0 | 0 | 100 | 0 | 100 | 30 | 0 | 40 | 30 |
| Green Foxtail | 100 | 100 | 0 | 100 | 0 | 100 | 100 | 100 | 95 | 100 | 100 | 100 | 100 | 90 | 100 | 10 | 40 | 0 |
| Johnsongrass | 100 | 100 | 50 | 80 | 0 | 100 | 95 | 70 | 20 | 0 | 70 | 90 | 0 | 100 | 80 | 20 | 40 | 60 |
| Yellow Nutsedge | 80 | 50 | 0 | 0 | 0 | 0 | 50 | 0 | 0 | 0 | 0 | 0 | 0 | 0 | 0 | 0 | 0 | 0 |

| Species | Compound No % Kill at 0.250 kg/ha | | | | | | | | | | | | | | | | |
|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 |
| Cotton | 0 | 0 | 0 | 0 | 0 | 0 | 0 | 0 | 0 | 0 | 0 | 0 | 0 | 0 | 0 | 0 | 0 |
| Soybean | 0 | 0 | 20 | 0 | 0 | 0 | 0 | 80 | 0 | 0 | 0 | 0 | 0 | 0 | 0 | 0 | 0 |
| Field Corn | 0 | 0 | 60 | 100 | 0 | 60 | 100 | 100 | 0 | 0 | 0 | 30 | 0 | 60 | 60 | 0 | 0 |
| Rice | 0 | 0 | 0 | 0 | 0 | 60 | 80 | 40 | 0 | 0 | 0 | 0 | 0 | 50 | 0 | 0 | 0 |
| Wheat | 0 | 0 | 0 | 0 | 0 | 30 | 90 | 95 | 0 | 0 | 0 | 0 | 0 | 50 | 0 | 0 | 100 |
| Field Bindweed | 0 | 0 | 0 | 0 | 0 | 60 | 50 | 100 | 0 | 0 | 0 | 0 | 0 | 0 | 0 | 0 | 0 |
| Morningglory | 0 | 0 | 0 | 0 | 0 | 0 | 0 | 70 | 0 | 0 | 0 | 0 | 0 | 0 | 0 | 0 | 0 |
| Velvetleaf | 0 | 70 | 50 | 80 | 0 | 90 | 90 | 100 | 0 | 0 | 0 | 70 | 0 | 90 | 0 | 0 | 100 |
| Barnyardgrass | 0 | 0 | 20 | 100 | 50 | 20 | 80 | 95 | 0 | 0 | 0 | 40 | 0 | 100 | 20 | 0 | 100 |
| Green Foxtail | 0 | 40 | 95 | 100 | 100 | 100 | 95 | 100 | 0 | 50 | 0 | 90 | 0 | 100 | 0 | 0 | 90 |
| Johnsongrass | 0 | 50 | 95 | 100 | 90 | 80 | 30 | 95 | 0 | 0 | 0 | 60 | 0 | 100 | 40 | 0 | 95 |
| Yellow Nutsedge | 0 | 0 | 0 | 0 | 0 | 0 | 0 | 0 | 0 | 0 | 0 | 0 | 0 | 0 | 0 | 0 | 0 |

TABLE 4

Preemergence Herbicidal Activity [2.000 kg/ha]

| Species | Compound No % Kill at 2.000 kg/ha | | | |
|---|---|---|---|---|
| | 36 | 37 | 38 | 39 |
| Cotton | 0 | 0 | 100 | 80 |
| Soybean | 0 | 0 | 100 | 100 |
| Field Corn | 100 | 0 | 100 | 100 |
| Rice | 100 | 0 | 100 | 100 |

TABLE 4-continued

Preemergence Herbicidal Activity [2.000 kg/ha]

| Species | Compound No % Kill at 2.000 kg/ha | | | |
|---|---|---|---|---|
| | 36 | 37 | 38 | 39 |
| Wheat | 100 | 0 | 100 | 100 |
| Field Bindweed | 100 | 0 | 100 | 100 |
| Morningglory | 90 | 0 | 100 | 100 |
| Velvetleaf | 100 | 0 | 100 | 100 |
| Barnyardgrass | 100 | 10 | 100 | 100 |
| Green Foxtail | 100 | 100 | 100 | 100 |
| Johnsongrass | 100 | 20 | 100 | 100 |
| Yellow Nutsedge | 80 | 0 | 100 | 100 |

TABLE 5

Postemergence Herbicidal Activity [4.000 kg/ha]

| Species | Compound No % Kill at 4.000 kg/ha | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Cotton | 100 | 80 | 90 | 100 | 20 | 60 | 95 | 100 | 100 | 10 | 60 | 100 | 100 | 100 | 100 | 100 | 80 |
| Soybean | 70 | 0 | 0 | 0 | 0 | 40 | 0 | 20 | 0 | 0 | 0 | 70 | 0 | 100 | 0 | 0 | 0 |
| Field Corn | 100 | 30 | 0 | 0 | 0 | 50 | 90 | 70 | 0 | 0 | 0 | 100 | 0 | 100 | 100 | 60 | 100 |
| Rice | 100 | 20 | 0 | 0 | 0 | 100 | 60 | 70 | 0 | 0 | 0 | 100 | 0 | 100 | 80 | 95 | 95 |
| Wheat | 100 | 40 | 60 | 0 | 0 | 60 | 70 | 80 | 0 | 0 | 0 | 95 | 0 | 100 | 100 | 100 | 100 |
| Field Bindweed | 100 | 30 | 30 | 40 | 0 | 100 | 80 | 95 | 0 | 50 | 0 | 100 | 100 | 100 | 90 | 80 | 80 |
| Morningglory | 100 | 90 | 40 | 20 | 30 | 90 | 100 | 100 | 50 | 40 | 0 | 100 | 10 | 100 | 90 | 100 | 100 |
| Velvetleaf | 100 | 100 | 100 | 100 | 90 | 100 | 100 | 100 | 100 | 100 | 100 | 100 | 100 | 100 | 100 | 100 | 100 |
| Barnyardgrass | 100 | 50 | 95 | 30 | 0 | 90 | 95 | 100 | 20 | 0 | 0 | 100 | 0 | 100 | 100 | 90 | 100 |
| Green Foxtail | 100 | 60 | 20 | 30 | 30 | 100 | 100 | 100 | 70 | 50 | 30 | 100 | 100 | 100 | 100 | 50 | 100 |
| Johnsongrass | 100 | 60 | 50 | 40 | 40 | 90 | 70 | 95 | 40 | 0 | 0 | 100 | 0 | 100 | 100 | 95 | 100 |
| Yellow Nutsedge | 80 | 0 | 0 | 0 | 0 | 40 | 60 | 95 | 0 | 0 | 0 | 10 | 0 | 0 | 0 | 0 | 50 |

| Species | Compound No % Kill at 4.000 kg/ha | | | | | | | | | | | | | | | | |
|---|---|---|---|---|---|---|---|---|---|---|---|---|---|---|---|---|---|
| | 18 | 19 | 20 | 21 | 22 | 23 | 24 | 25 | 27 | 28 | 29 | 30 | 31 | 32 | 33 | 34 | 35 |
| Cotton | 80 | 50 | 80 | 100 | 100 | 40 | 100 | 100 | 20 | 80 | 70 | 80 | 100 | 100 | 80 | 60 | 100 |
| Soybean | 60 | 0 | 80 | 100 | 0 | 0 | 50 | 20 | 0 | 0 | 0 | 0 | 30 | 20 | 0 | 0 | 0 |
| Field Corn | 100 | 0 | 30 | 100 | 60 | 0 | 100 | 100 | 0 | 0 | 0 | 0 | 0 | 100 | 100 | 0 | 0 |
| Rice | 70 | 0 | 0 | 100 | 90 | 10 | 80 | 90 | 0 | 0 | 0 | 70 | 20 | 100 | 20 | 0 | 0 |
| Wheat | 100 | 30 | 100 | 100 | 100 | 30 | 95 | 100 | 0 | 80 | 0 | 20 | 0 | 100 | 100 | 40 | 100 |
| Field Bindweed | 70 | 0 | 90 | 100 | 100 | 100 | 100 | 100 | 0 | 80 | 0 | 80 | 60 | 100 | 100 | 80 | 0 |
| Morningglory | 80 | 40 | 80 | 100 | 90 | 10 | 100 | 100 | 0 | 10 | 70 | 80 | 40 | 100 | 100 | 50 | 0 |
| Velvetleaf | 100 | 90 | 100 | 100 | 100 | 90 | 100 | 100 | 80 | 100 | 30 | 90 | 100 | 100 | 100 | 100 | 100 |
| Barnyardgrass | 100 | 40 | 0 | 100 | 100 | 10 | 90 | 100 | 0 | 0 | 0 | 95 | 0 | 100 | 95 | 0 | 100 |
| Green Foxtail | 100 | 70 | 80 | 100 | 100 | 90 | 100 | 100 | 80 | 100 | 95 | 100 | 100 | 100 | 100 | 0 | 90 |
| Johnsongrass | 100 | 10 | 90 | 100 | 100 | 30 | 100 | 100 | 0 | 70 | 0 | 100 | 0 | 100 | 100 | 0 | 100 |
| Yellow Nutsedge | 50 | 0 | 0 | 100 | 0 | 0 | 10 | 90 | 0 | 0 | 0 | 0 | 0 | 100 | 0 | 0 | 0 |

TABLE 6

Postemergence Herbicidal Activity [2.000 kg/ha]

| Species | Compound No % Kill at 2.000 kg/ha | | | |
|---|---|---|---|---|
| | 36 | 37 | 38 | 39 |
| Cotton | 100 | 0 | 100 | 100 |
| Soybean | 0 | 0 | 90 | 90 |
| Field Corn | 60 | 0 | 100 | 100 |
| Rice | 95 | 0 | 100 | 100 |
| Wheat | 100 | 0 | 100 | 100 |
| Field Bindweed | 90 | 70 | 100 | 100 |
| Morningglory | 100 | 50 | 100 | 100 |
| Velvetleaf | 100 | 0 | 100 | 100 |
| Barnyardgrass | 90 | 0 | 100 | 100 |
| Green Foxtail | 100 | — | 100 | 100 |
| Johnsongrass | 100 | 0 | 100 | 100 |
| Yellow Nutsedge | 0 | 0 | 100 | 100 |

It is clear that the generic class of aryltriazolinones and sulfur analogs thereof described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal applications, the active compounds as above defined are formulated into herbicidal compositions, by admixture, in herbicidally effective amounts, with the adjuvants and carriers normally employed for facilitating the dispersion of active ingredients for the particular utility desired, recognizing the fact that the formulation and mode of application of a toxicant may affect the activity of the material in a given application. Thus, these active herbicidal compounds may be formulated as granules of relatively large particle size, as water-soluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules in the area in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation, useful herein, is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank mix for postemergence application to facilitate dispersion on the foliage and absorption by the plant.

Other useful formulations for herbicidal applications are emulsifiable concentrates, which are homogeneous liquid or paste compositions which are dispersible in water or other dispersant, and may consist entirely of the herbicidal compound and a liquid or solid emulsifying agent, or may also contain a liquid carrier, such as xylene, heavy aromatic naphthas, isophorone, and other non-volatile organic solvents. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises from 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442, incorporated herein by reference, are useful herein with the present herbicidal compounds.

The active herbicidal compounds of this invention may be formulated and/or applied with insecticides, fungicides, nematocides, plant growth regulators, fertilizers, and other agricultural chemicals and may be used as effective soil sterilants as well as herbicidally. In applying an active compound of this invention, whether formulated alone or with other agricultural chemicals, an effective amount and concentration of the compound is of course employed.

It is apparent that various modifications may be made in the formulation and application of the novel compounds of this invention, without departing from the inventive concepts herein, as defined in the following claims.

I claim:

1. An herbicidal compound of the formula

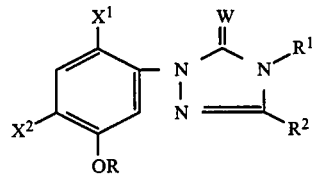

in which
 $X^1$ is fluorine,
 $X^2$ is chlorine or bromine,
 W is oxygen,
 $R^1$ is n-propyl, difluoromethyl, 3-fluoropropyl, cyanomethyl, or 2-propenyl,
 $R^2$ is methyl, fluoromethyl, or difluoromethyl, and
 R is 3-tetrahydrofuranyl, tetrahydrofurfuryl, tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 1,3-dioxan-4-ylmethyl, tetrahydro-4H-pyran-4-yl, tetrahydrothien-3-yl, 1-oxotetrahydrothien-3-yl, or 1,1-dioxotetrahydrothien-3-yl.

2. The compound of claim 1 in which $R^1$ is difluoromethyl and $R^2$ is methyl.

3. The compound of claim 2 in which R is 3-tetrahydrofuranyl, tetrahydrofurfuryl, or 1,1-dioxotetrahydrothien-3-yl.

4. The compound of claim 3 in which $X^2$ is chlorine.

5. An herbicidal composition comprising an herbicidally effective amount of a compound of claim 1 in admixture with a suitable inert carrier.

6. A method for controlling undesired plant growth which comprises applying to the locus where control is desired an herbicidally effective amount of the composition of claim 5.

7. The method of claim 6 in which the locus where control is desired is planted or to be planted with soybeans, corn, or cotton.

8. The method of claim 7 in which the locus where control is desired is planted or to be planted with soybeans.

* * * * *